US006743321B2

(12) United States Patent
Guralski et al.

(10) Patent No.: US 6,743,321 B2
(45) Date of Patent: Jun. 1, 2004

(54) METHOD AND APPARATUS FOR ASSEMBLING REFASTENABLE ABSORBENT GARMENTS

(75) Inventors: Daniel M. Guralski, Reedsville, WI (US); Donald J. Sanders, Larsen, WI (US); David H. Swanton, Hortonville, WI (US); Paul T. Van Gompel, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 315 days.

(21) Appl. No.: 09/954,444

(22) Filed: Sep. 14, 2001

(65) Prior Publication Data

US 2003/0135192 A1 Jul. 17, 2003

(51) Int. Cl.⁷ .................. B32B 31/18; A41H 37/00; A44B 19/00; B29C 58/40; A61F 5/44
(52) U.S. Cl. .................. 156/250; 156/66; 156/217; 156/204; 156/252; 156/264; 156/269; 604/389; 604/390; 604/391; 428/401; 428/74; 428/79
(58) Field of Search .................. 156/66, 204, 227, 156/269, 252, 270, 226, 256, 290, 304.2, 304.3, 308.4, 216, 250, 217; 604/390, 385.3, 391, 394, 387, 461, 389; 428/74, 78, 79, 195, 206, 40.1, 41.8, 42.3, 343

(56) References Cited

U.S. PATENT DOCUMENTS

| 3,663,962 A | 5/1972 | Burger |
| 3,828,367 A | 8/1974 | Bourgeois |
| 3,874,032 A | 4/1975 | Simon et al. |
| 4,253,461 A | * 3/1981 | Strickland et al. .......... 604/389 |
| 4,409,052 A | 10/1983 | von Agris et al. |
| 4,608,115 A | 8/1986 | Schroth et al. |
| 4,615,695 A | 10/1986 | Cooper |
| 4,647,336 A | 3/1987 | Coenen et al. |
| 4,650,530 A | 3/1987 | Mahoney et al. |
| D290,780 S | 7/1987 | Wistrand |
| 4,713,132 A | 12/1987 | Abel et al. |

(List continued on next page.)

FOREIGN PATENT DOCUMENTS

| DE | 198 13 334 A1 | 9/1999 |
| EP | 0 396 512 A2 | 11/1990 |
| EP | 0528 282 A2 | 2/1993 |
| EP | 0 570 980 | 11/1993 |
| EP | 0 591 647 B1 | 4/1994 |

(List continued on next page.)

OTHER PUBLICATIONS

U.S. patent application Ser. No. 09/954,444, entitled "Method and Apparatus for Assembling Refastenable Absorbent Garments," filed on Sep. 14, 2001 (659–876).
U.S. patent application Ser. No. 09/954,478 entitled "Method and Apparatus for Assembling Refastenable Absorbent Garments," filed Sep. 14, 2001 (659–874).

(List continued on next page.)

Primary Examiner—J. A. Lorengo
(74) Attorney, Agent, or Firm—Brinks Hofer Gilson & Lione

(57) ABSTRACT

A method for fabricating a refastenable absorbent garment includes moving a continuous body panel web in a machine direction and successively fixedly securing a plurality of discrete fastener pieces, spaced along the machine direction, to the body panel web. Each of the fastener pieces comprises a first and second end also spaced along the machine direction. The method further includes successively cutting said body panel web and each of the fastener pieces along a cross direction between the first and second ends of each of the fastener pieces and thereby forming a plurality of discrete body panels each comprising opposite side edges and a plurality of pairs of fastener members fixedly secured to one of the plurality of body panels and a next successive body panel.

39 Claims, 10 Drawing Sheets

U.S. PATENT DOCUMENTS

| | | |
|---|---|---|
| 4,743,241 A | 5/1988 | Igaue et al. |
| 4,758,293 A | 7/1988 | Samida |
| 4,801,298 A | 1/1989 | Sorenson et al. |
| 4,847,134 A | 7/1989 | Fahrenkrug et al. |
| 4,906,243 A | 3/1990 | Dravland |
| 4,960,414 A | 10/1990 | Meyer |
| 4,998,929 A | 3/1991 | Bjorksund et al. |
| 5,080,741 A | 1/1992 | Nomura et al. |
| 5,087,253 A | 2/1992 | Cooper |
| 5,096,532 A | 3/1992 | Neuwirth et al. |
| 5,110,403 A | 5/1992 | Ehlert |
| 5,145,351 A | 9/1992 | Rossi |
| 5,147,487 A | 9/1992 | Nomura et al. |
| 5,221,390 A | 6/1993 | Persson et al. |
| 5,235,515 A | 8/1993 | Ungpiyakul et al. |
| 5,242,436 A | 9/1993 | Weil et al. |
| 5,286,543 A | 2/1994 | Ungpiyakul et al. |
| 5,340,424 A | 8/1994 | Matsushita |
| 5,370,634 A | 12/1994 | Ando et al. |
| 5,376,198 A | 12/1994 | Fahrenkrug et al. |
| 5,415,649 A | 5/1995 | Watanabe et al. |
| 5,449,353 A | 9/1995 | Watanabe et al. |
| 5,454,803 A | 10/1995 | Sageser et al. |
| 5,500,063 A | 3/1996 | Jessup |
| 5,540,796 A | 7/1996 | Fries |
| 5,542,943 A | 8/1996 | Sageser |
| 5,552,007 A | 9/1996 | Rajala et al. |
| 5,552,013 A | 9/1996 | Ehlert et al. |
| 5,554,145 A | 9/1996 | Roe et al. |
| 5,556,504 A | 9/1996 | Rajala et al. |
| 5,562,790 A | 10/1996 | Ehlert et al. |
| 5,569,234 A | 10/1996 | Buell et al. |
| 5,578,152 A * | 11/1996 | Goulait et al. ................. 156/66 |
| 5,582,606 A | 12/1996 | Bruemmer et al. |
| 5,591,155 A | 1/1997 | Nishikawa et al. |
| 5,601,547 A | 2/1997 | Kato et al. |
| 5,609,702 A | 3/1997 | Andersen |
| 5,624,420 A | 4/1997 | Bridges et al. |
| 5,643,377 A | 7/1997 | Juergens |
| 5,643,396 A | 7/1997 | Rajala et al. |
| 5,659,229 A | 8/1997 | Rajala |
| 5,660,657 A | 8/1997 | Rajala et al. |
| 5,660,679 A | 8/1997 | Rajala et al. |
| 5,667,608 A | 9/1997 | Rajala et al. |
| 5,683,376 A | 11/1997 | Kato et al. |
| 5,685,873 A | 11/1997 | Bruemmer |
| 5,685,874 A | 11/1997 | Buell et al. |
| RE35,687 E | 12/1997 | Igaue et al. |
| 5,707,364 A | 1/1998 | Coates |
| 5,707,470 A | 1/1998 | Rajala et al. |
| 5,711,832 A | 1/1998 | Glaug et al. |
| 5,711,847 A | 1/1998 | Rajala et al. |
| 5,716,478 A | 2/1998 | Boothe et al. |
| 5,733,411 A | 3/1998 | Bett |
| 5,745,922 A | 5/1998 | Rajala et al. |
| 5,749,866 A | 5/1998 | Roe et al. |
| 5,749,989 A | 5/1998 | Linman et al. |
| 5,759,340 A | 6/1998 | Boothe et al. |
| 5,766,389 A | 6/1998 | Brandon et al. |
| 5,817,199 A | 10/1998 | Brennecke et al. |
| 5,836,931 A | 11/1998 | Toyoda et al. |
| 5,855,574 A | 1/1999 | Kling et al. |
| 5,858,151 A | 1/1999 | Igaue et al. |
| 5,858,515 A | 1/1999 | Stokes et al. |
| 5,879,500 A | 3/1999 | Herrin et al. |
| 5,897,545 A | 4/1999 | Kline et al. |
| 5,904,673 A | 5/1999 | Roe et al. |
| 5,940,887 A | 8/1999 | Rajala et al. |
| 5,957,908 A | 9/1999 | Kline et al. |
| 6,022,431 A | 2/2000 | Blenke et al. |
| 6,022,432 A | 2/2000 | Elsberg et al. |
| 6,036,805 A | 3/2000 | McNichols |
| 6,077,379 A | 6/2000 | Herrin et al. |
| 6,098,203 A | 8/2000 | Rajala et al. |
| 6,099,516 A * | 8/2000 | Pozniak et al. .............. 604/386 |
| 6,113,717 A | 9/2000 | Vogt et al. |
| 6,132,410 A | 10/2000 | Van Gompel et al. |
| 6,132,411 A | 10/2000 | Huber et al. |
| 6,139,004 A | 10/2000 | Couillard et al. |
| 6,197,138 B1 | 3/2001 | McNichols |
| 6,210,388 B1 | 4/2001 | Widlund et al. |
| 6,217,563 B1 | 4/2001 | Van Gompel et al. |
| 6,217,690 B1 | 4/2001 | Rajala et al. |
| 6,227,541 B1 | 5/2001 | Couillard et al. |
| 6,240,569 B1 | 6/2001 | Van Gompel et al. |
| 6,264,641 B1 | 7/2001 | Van Gompel et al. |
| 6,328,725 B2 * | 12/2001 | Fernfors ..................... 604/391 |
| 6,336,922 B1 | 1/2002 | VanGompel et al. |
| 6,361,527 B1 | 3/2002 | Van Gompel et al. |
| 6,375,646 B1 | 4/2002 | Widlund et al. |
| 6,395,115 B1 * | 5/2002 | Popp et al. .................... 156/66 |
| 6,409,858 B1 * | 6/2002 | Popp et al. .................... 156/66 |
| 6,454,751 B1 * | 9/2002 | Olson ........................ 604/389 |
| 6,478,786 B1 | 11/2002 | Glaug et al. |

FOREIGN PATENT DOCUMENTS

| | | |
|---|---|---|
| EP | 0 630 221 B2 | 12/1994 |
| EP | 0 719 534 B1 | 7/1996 |
| EP | 0 934 739 A2 | 8/1999 |
| EP | 1 013 251 A1 | 6/2000 |
| EP | 1 027 874 A2 | 8/2000 |
| EP | 1 062 930 A2 | 12/2000 |
| EP | 1 066 811 | 1/2001 |
| EP | 0 907 510 B1 | 3/2002 |
| GB | 2 288 316 | 11/1997 |
| GB | 2 311 249 | 7/1999 |
| JP | 03176053 A | 7/1991 |
| JP | 3-205053 | 9/1991 |
| JP | 4-22359 | 1/1992 |
| WO | WO 95/22306 | 8/1995 |
| WO | WO 95/27461 | 10/1995 |
| WO | WO 95/27462 | 10/1995 |
| WO | WO 96/14039 | 5/1996 |
| WO | WO 96/23466 | 8/1996 |
| WO | WO 96/23467 | 8/1996 |
| WO | WO 96/38112 | 12/1996 |
| WO | WO 97/02795 | 1/1997 |
| WO | WO 97/02797 | 1/1997 |
| WO | WO 97/02799 | 1/1997 |
| WO | WO 97/23180 | 7/1997 |
| WO | WO 97/46197 | 12/1997 |
| WO | WO 97/48357 | 12/1997 |
| WO | WO 98/27921 | 7/1998 |
| WO | WO 99/33425 | 7/1999 |
| WO | WO 00 20208 | 4/2000 |
| WO | WO 00/37009 | 6/2000 |
| WO | WO 01/13843 | 3/2001 |
| WO | WO 01/13844 | 3/2001 |
| WO | WO 01/13845 | 3/2001 |
| WO | WO 01/13846 | 3/2001 |
| WO | WO 01/13847 | 3/2001 |
| WO | WO 01/13848 | 3/2001 |
| WO | WO 01/13849 | 3/2001 |
| WO | WO 01/13850 | 3/2001 |
| WO | WO 01/13851 | 3/2001 |
| WO | WO 01/43682 A1 | 6/2001 |
| WO | WO 02/083048 A1 | 10/2002 |
| WO | WO 02/083049 A1 | 10/2002 |
| WO | WO 02/083050 A1 | 10/2002 |

OTHER PUBLICATIONS

U.S. patent application Ser. No. 09/954,480 entitled "Method and Apparatus for Assembling Refastenable Absorbent Garments," filed Sep. 14, 2001 (659–878)

U.S. patent application Ser. No. 09/637,432 entitled "Refastenable Absorbent Article Exhibiting Improved Body Fit," filed on Aug. 11, 2000 (KC 16098).

U.S. patent application Ser. No. 09/637,430 entitled "Refastenable Absorbent Article Exhibiting Improved Body Fit," filed Aug. 11, 2000 (KC 16099).

U.S. patent application Ser. No. 09/637,431 entitled "Refastenable Absorbent Article Exhibiting Improved Body Fit," filed Aug. 11, 2000 (KC 16100).

U.S. patent application Ser. No. 09/637,429 entitled "Absorbent Article Having a Refastenable Mechanism," filed Aug. 11, 2000 (KC 16101).

U.S. patent application Ser. No. 09/637,428 entitled "Absorbent Article Having a Refastenable Mechanism," filed Aug. 11, 2000 (KC 16102).

U.S. patent application Ser. No. 09/637,427 entitled "Absorbent Article Having a Refastenable Mechanism," filed Aug. 11, 2000 (KC 16103).

U.S. patent application Ser. No. 09/637,423 entitled Absorbent Article Having a Refastenable Mechanism, filed Aug. 11, 2000 (KC 16104).

U.S. patent application Ser. No. 09/637,424 entitled "Absorbent Article Having a Refastenable Mechanism," filed Aug. 11, 2000 (KC 16105).

U.S. patent application Ser. No. 09/637,425 entitled "Absorbent Article Having a Refastenable Mechanism," filed Aug. 11, 2000 (KC 16106).

U.S. patent application Ser. No. 09/637,426 entitled "Absorbent Article Exhibiting Improved Body Fit," filed Aug. 11, 2000 (KC 16107).

U.S. patent application entitled "Methods of Changing Size of Pant–Type Personal Care Articles Outputted From a Manufacturing Process," filed Apr. 13, 2001 (14755).

U.S. patent application Ser. No. 09/834,869 entitled "Pant–Type Personal Care Articles, and Methods of Making and Using Such Personal Care Articles," filed Apr. 13, 2001 (KC 14754).

U.S. patent application Ser. No. 09/834,870 entitled "Passive Bonds for Personal Care Article," filed Apr. 13, 2001 (KC 15412).

U.S. patent application Ser. No. 09/834,870 entitled "Multiple Component Web," filed Apr. 13, 2001 (KC 15649).

U.S. patent application Ser. No. 09/834,875 entitled "Method of Assembling Personal Care Absorbent Article," filed Apr. 13, 2001 (KC 15490).

U.S. Provisional patent application Ser. No. 60/150,382 entitled "Pants, Refastenable Pants/Undergarments/Briefs Product Design and Process for Manufacturing on a Single Asset," filed Aug. 23, 1999 (KC 14509).

U.S. Provisional patent application Ser. No. 60/150,327 entitled "Refastenable Pant with Perforated Front Panels," filed Aug. 23, 1999 (KC 14647).

U.S. patent application S/N 09/002,020, entitled "Personal Care Article Having a Stretch Outer Cover and Non–Stretch Grasping Panels," filed Dec. 31, 1997 (KC 12,221).

International Search Report in corresponding PCT Application No. PCT/US02/24681, dated May 23, 2003, 8 pages.

* cited by examiner

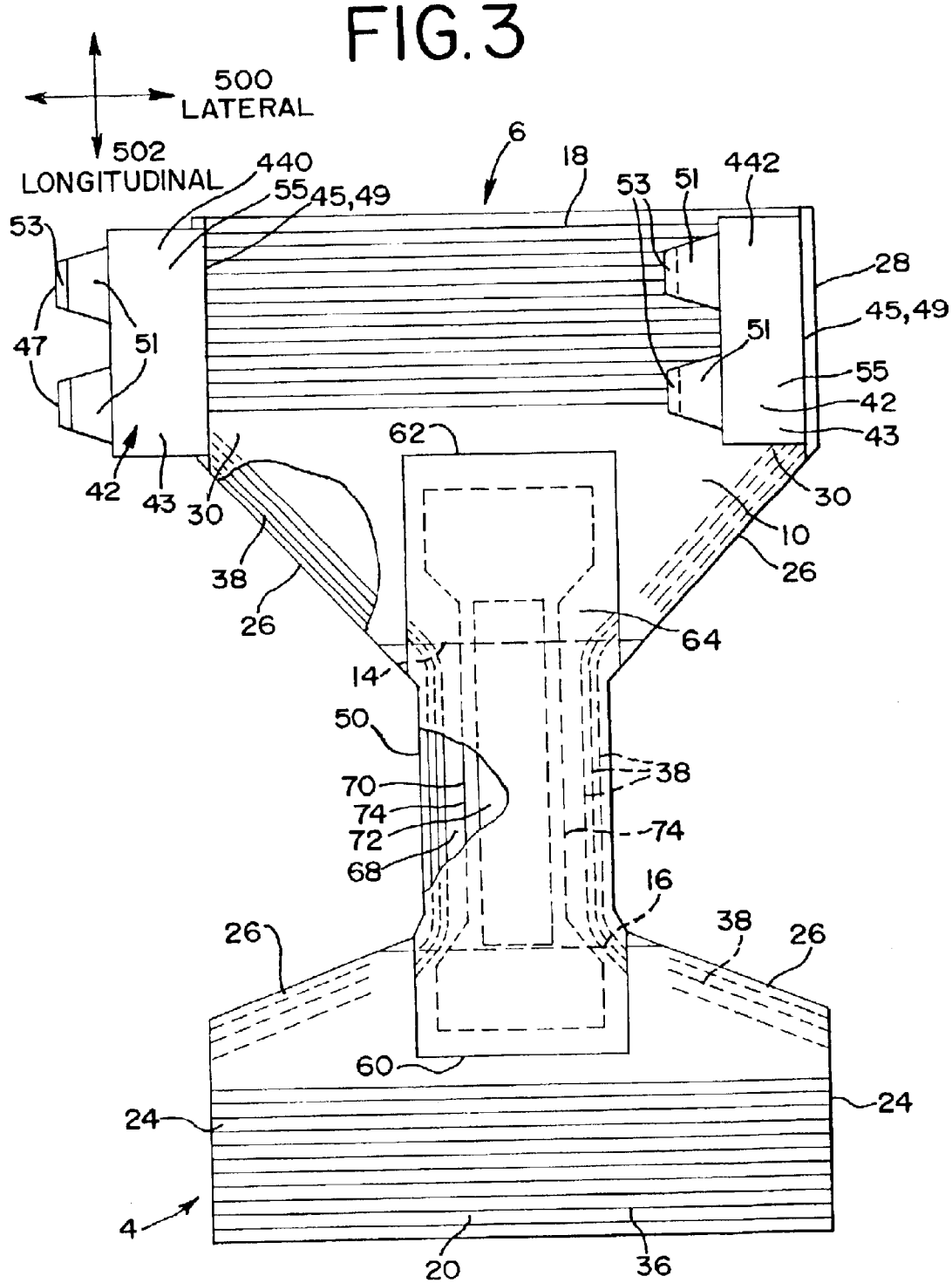

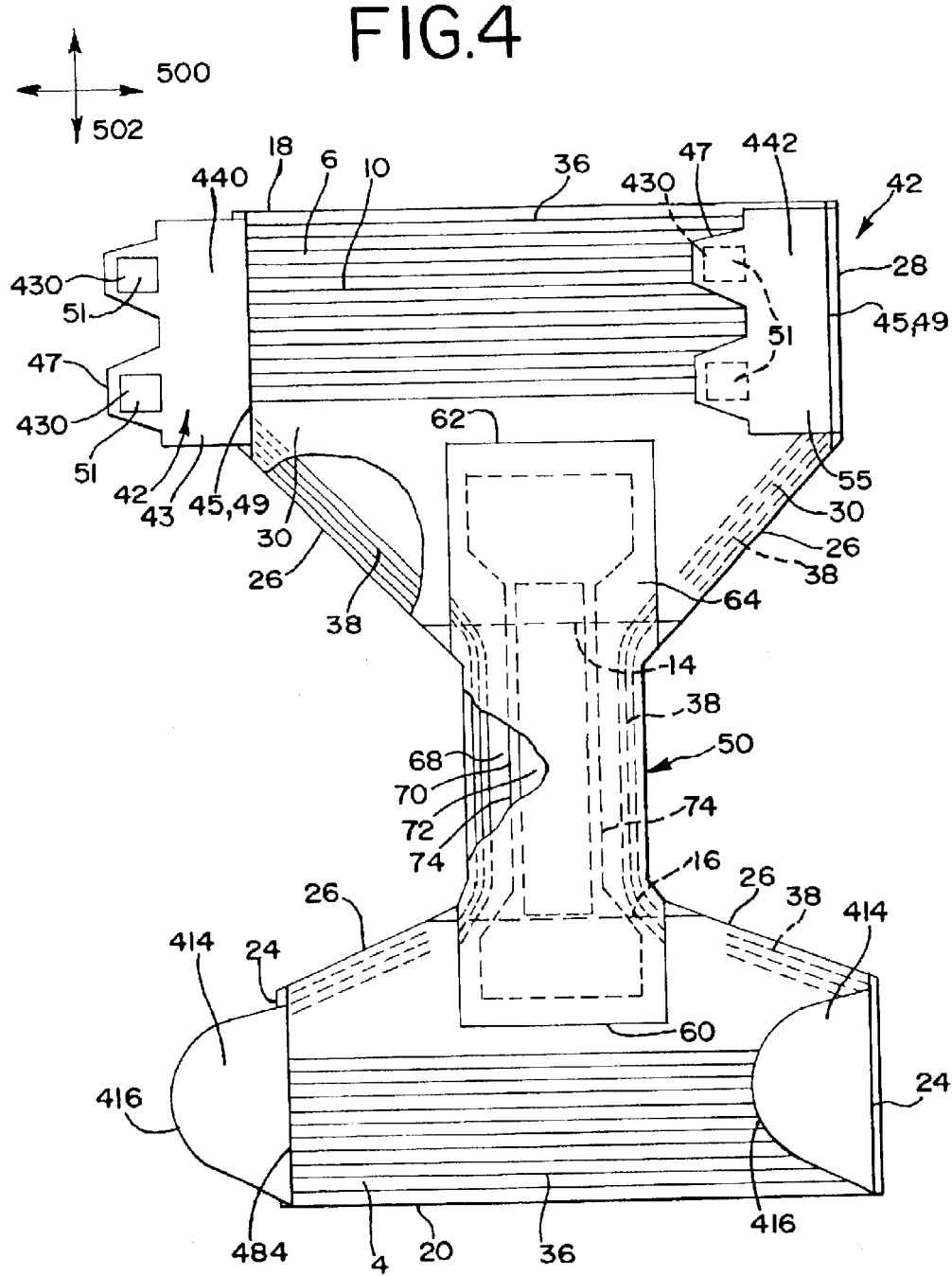

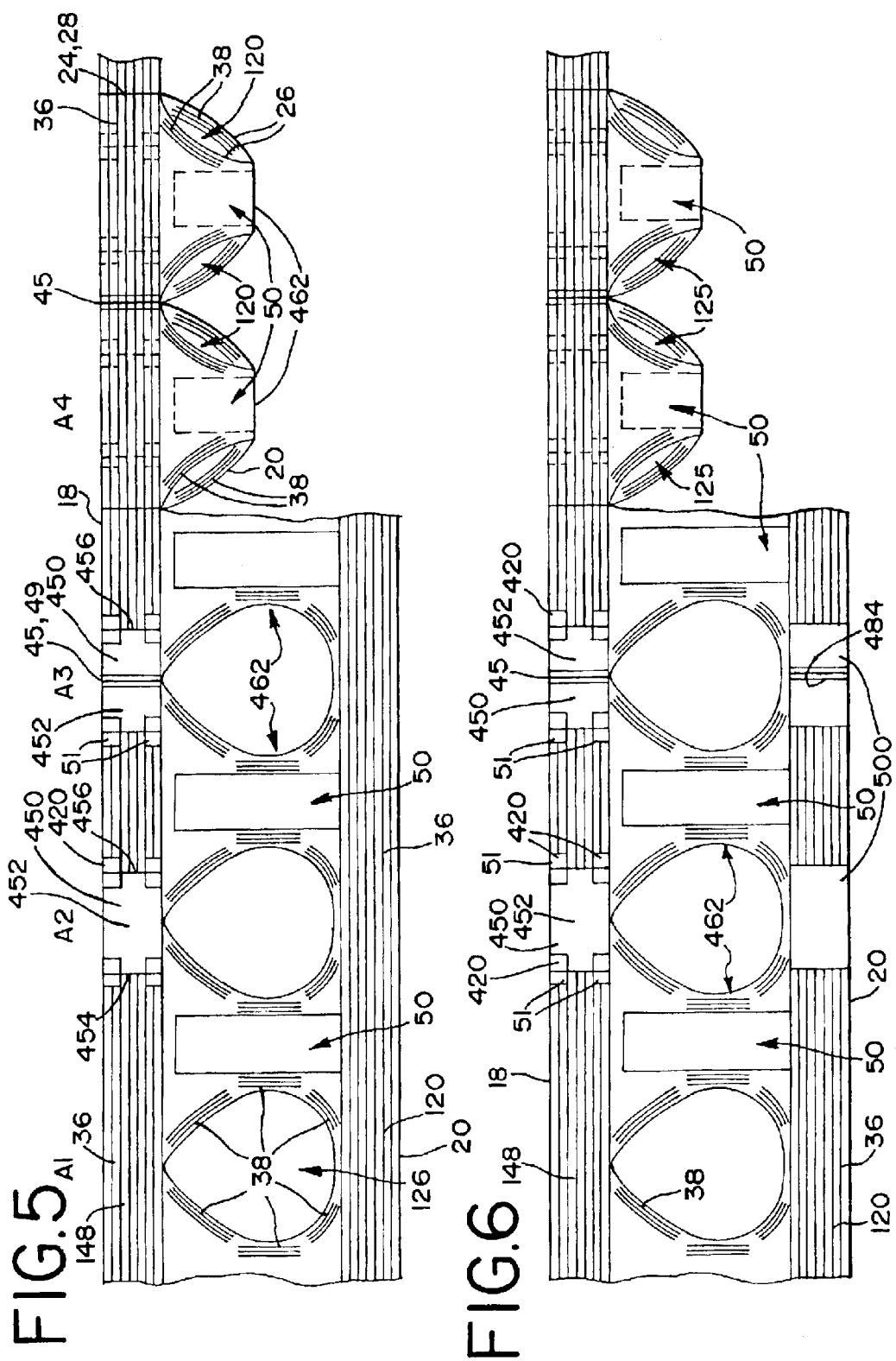

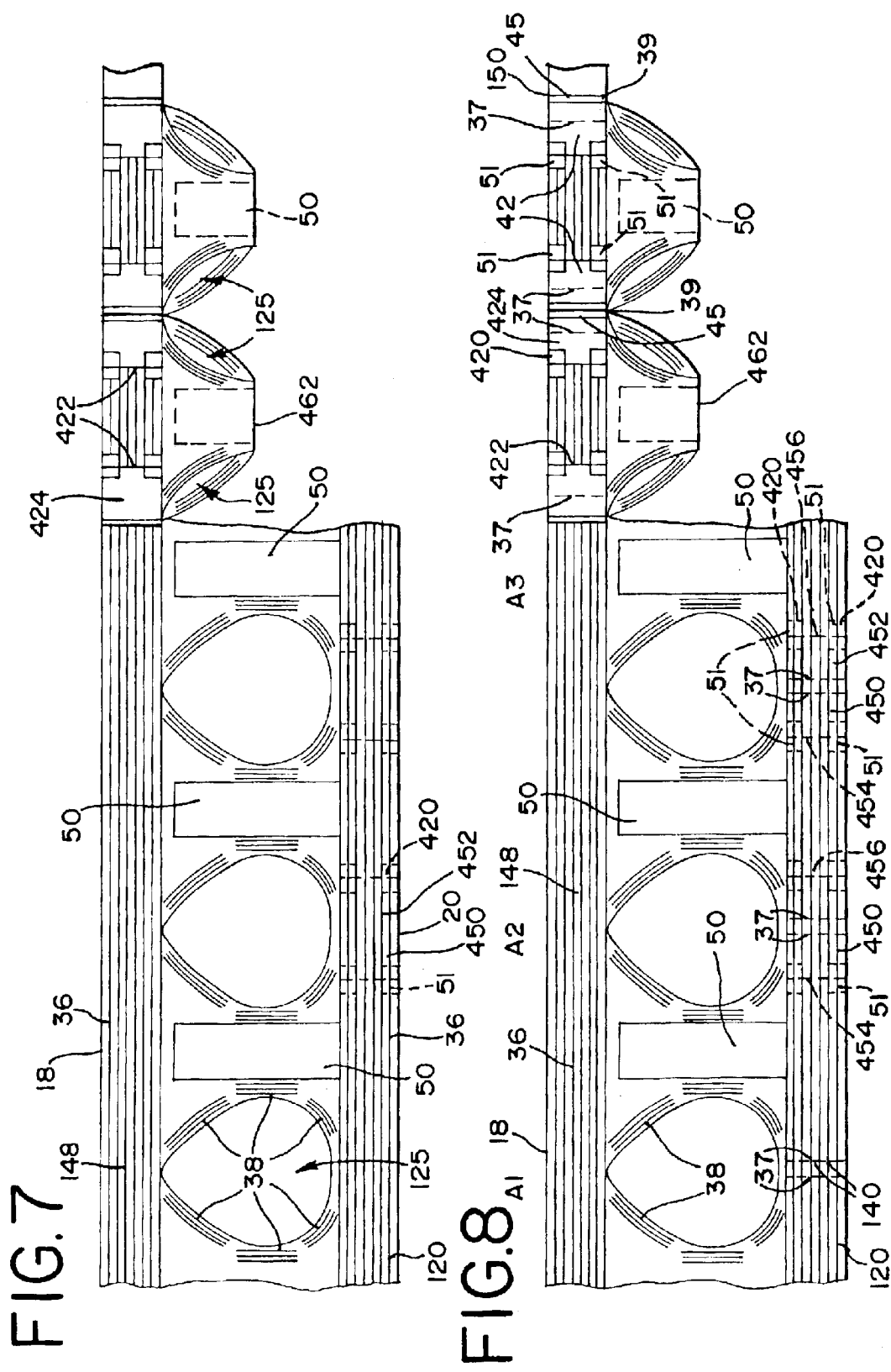

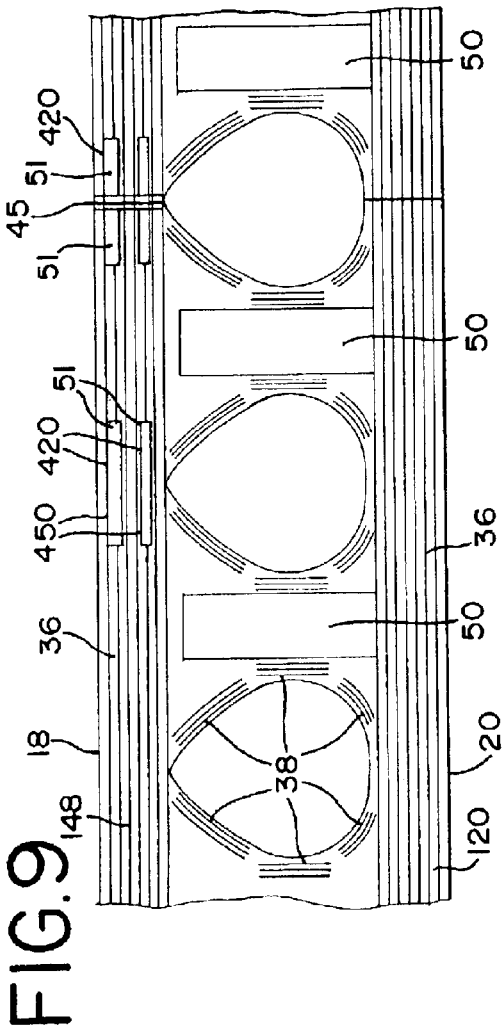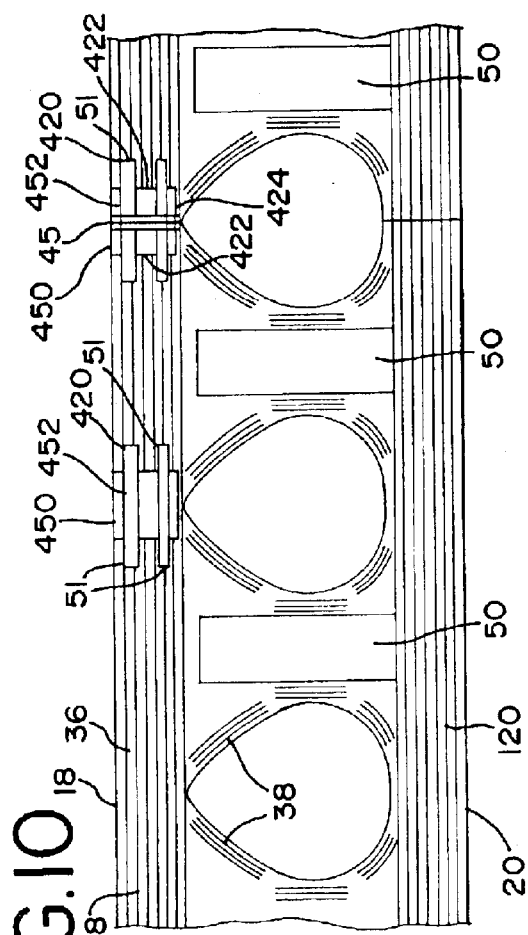

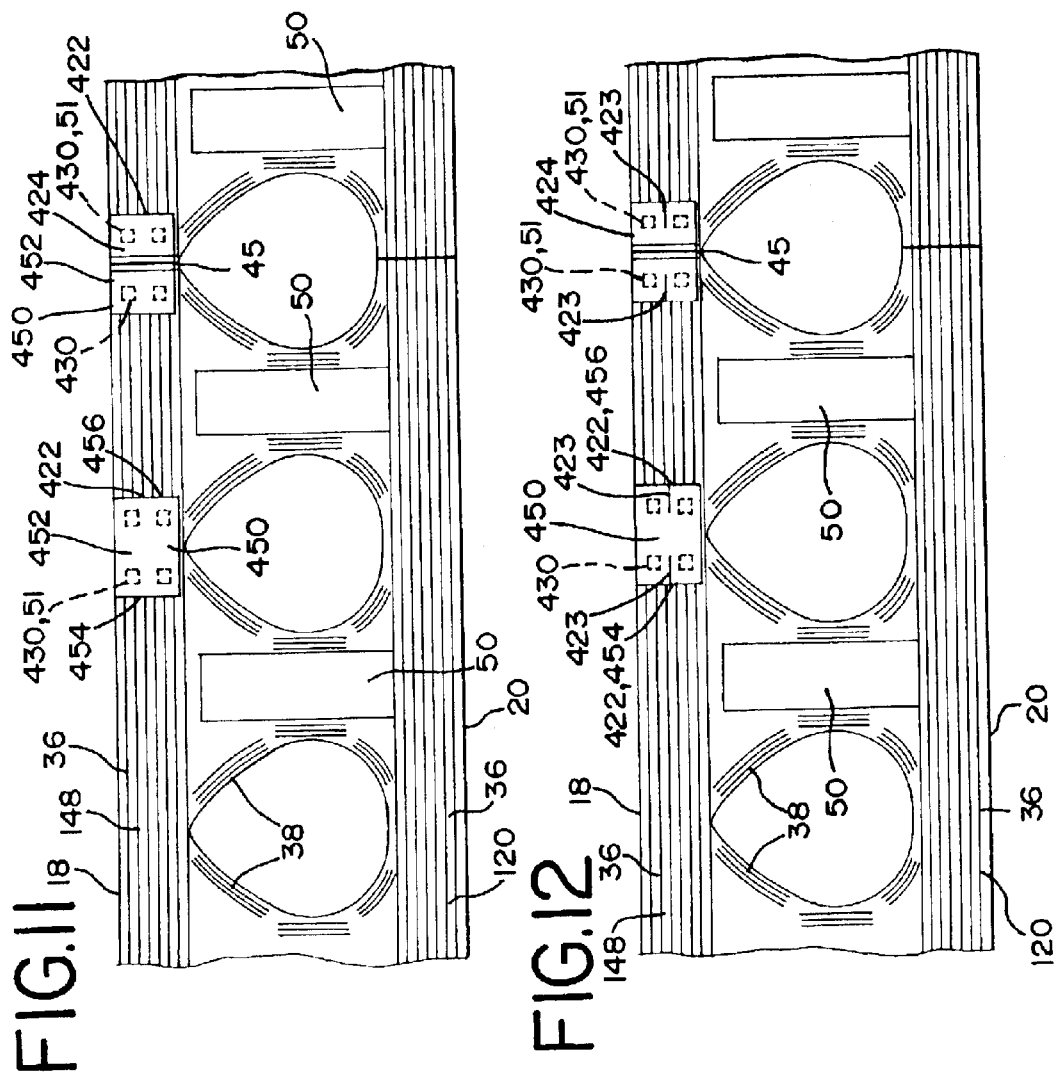

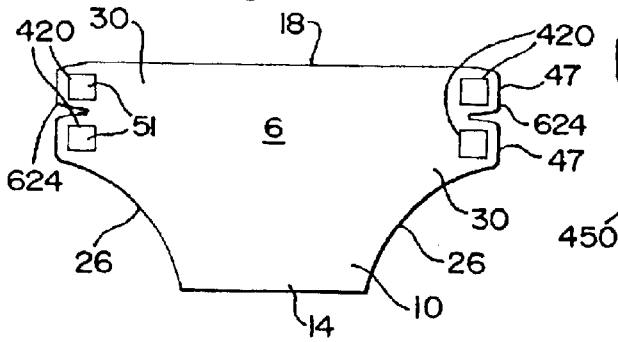
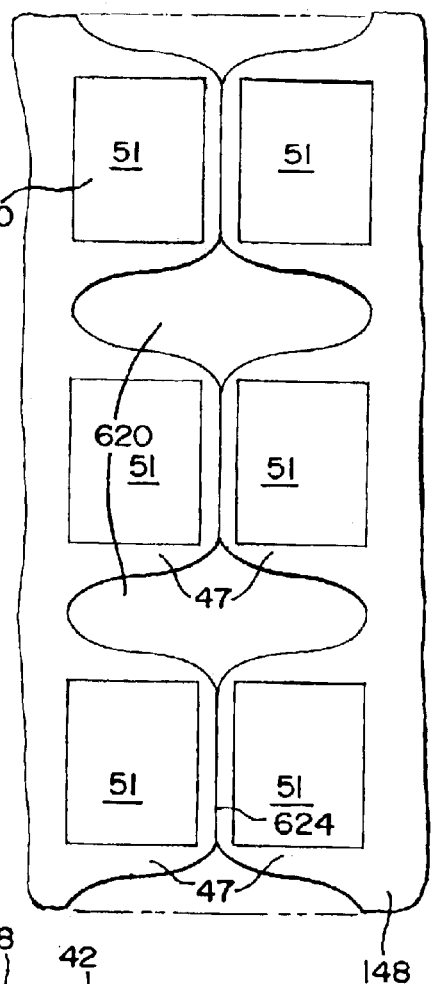
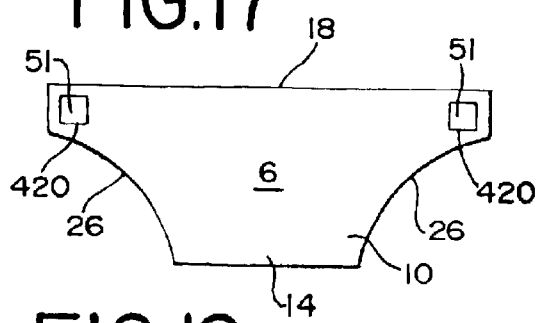
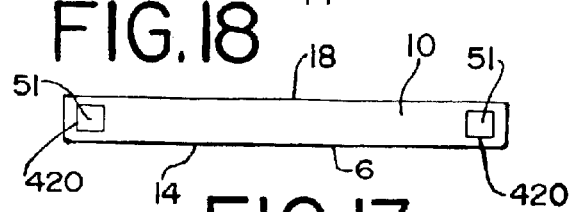
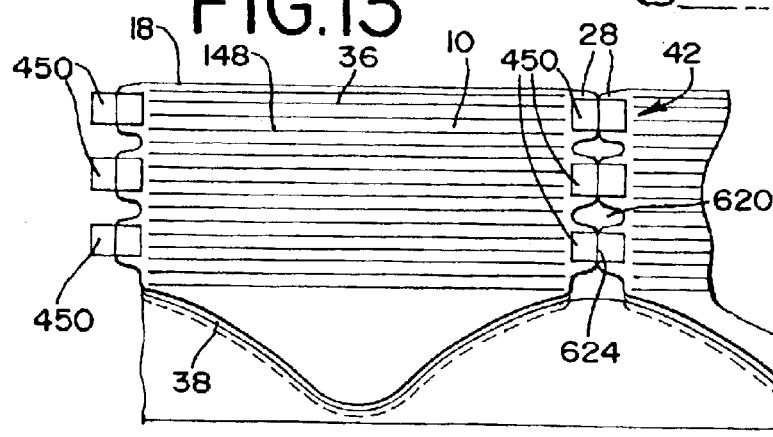
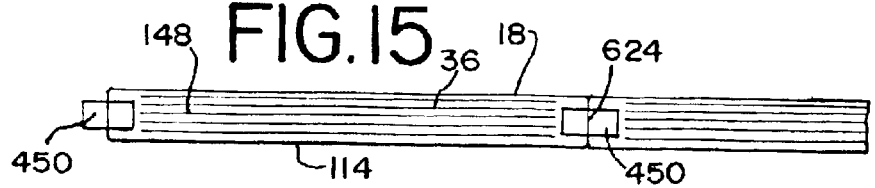

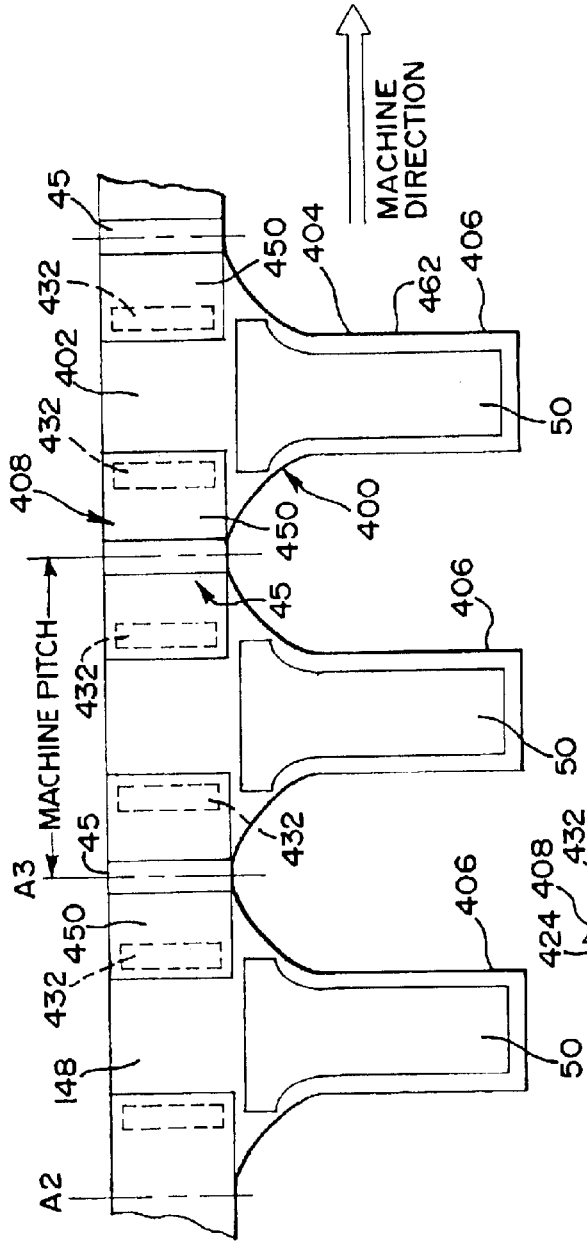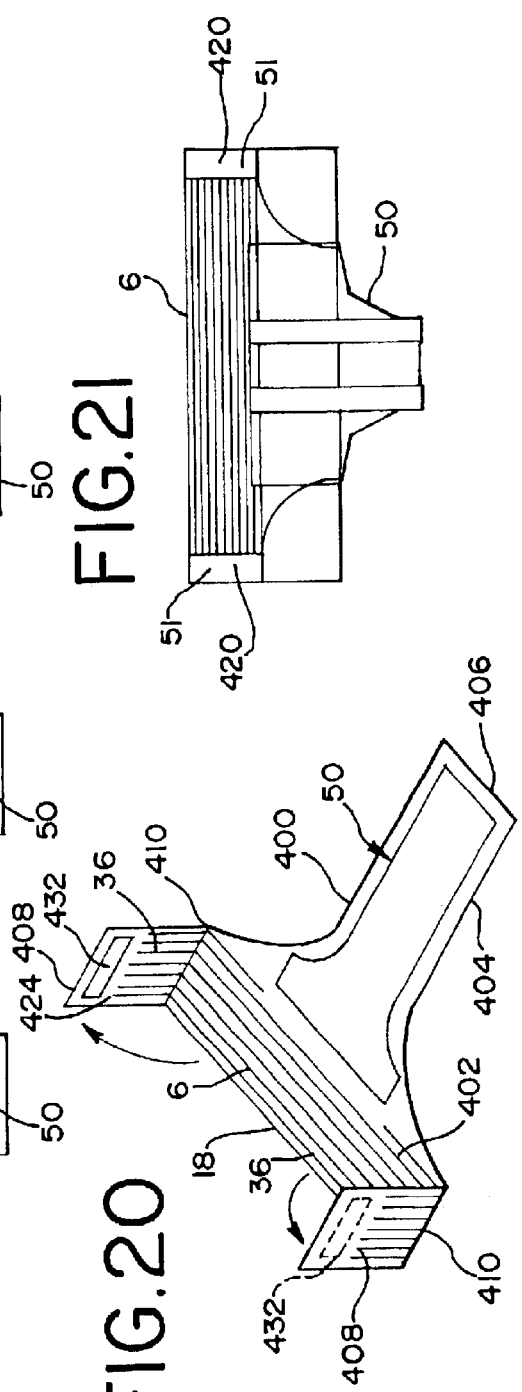

METHOD AND APPARATUS FOR ASSEMBLING REFASTENABLE ABSORBENT GARMENTS

BACKGROUND

The present invention relates generally to a refastenable absorbent garment, and in particular, to a method for fabricating refastenable absorbent garments.

Absorbent garments can be configured in many different forms. For example, absorbent garments can be configured as a pant-type, pull-on garment, or as a diaper-type product that is drawn up between the legs and fastened about the waist with various fastening systems. Pant-type, pull-on garments are often provided with various elastic elements that can conform to the body of the user and provide a comfortable, snug fit. Such garments, however, often do not have a refastenable mechanism that allows the garment to be easily removed after use or to be adjusted during use.

On the other hand, diaper-type products, which can be configured with fastening systems that allow the user to detach and reattach various fasteners so as to provide a refastenable absorbent garment, often are not configured with various elastic elements, for example around the waist, and may not conform well to the body of the user and/or may provide a bulky appearance beneath the user's garments. Moreover, such garments are typically produced as an "open" product, which is open at the sides and which cannot be pulled on like a pant-type garment. Some consumers prefer a pull-on type garment, since the garment is applied to the user like conventional underwear. Therefore, there remains a need for an improved absorbent garment, and in particular a pant-type garment, that is refastenable and provides a snug fit with a non-bulky appearance.

In addition, manufacturing facilities are often configured to fabricate one particular type of product. As such, these facilities may not provide the flexibility to transition between fabricating a conventional pull-on type garment and fabricating a refastenable garment using a single manufacturing line or asset. Therefore the need also remains for improved methods and assemblies for manufacturing refastenable absorbent garments.

SUMMARY

Briefly stated, in one aspect, the invention is directed to a method for assembling a refastenable absorbent garment. In one preferred embodiment, the method includes moving a continuous body panel web in a machine direction and successively fixedly securing a plurality of discrete fastener pieces, spaced along the machine direction, to the body panel web. Each of the fastener pieces includes a first and second end also spaced along the machine direction. The method further includes successively cutting the body panel web and each of the fastener pieces along a cross direction at a location between the first and second ends of each of the fastener pieces and thereby forming a plurality of discrete body panels each comprising opposite side edges and a plurality of pairs of fastener members fixedly secured to one of the plurality of body panels and a next successive body panel.

In one preferred embodiment, each of said fastener pieces includes a refastenable portion formed proximate at least both of the first and second ends thereof. In one preferred embodiment, the method further includes releasably engaging the body panel web with the refastenable portions of each of the plurality of discrete fastener pieces.

In another aspect, the method further includes successively cutting, and preferably perforating, the body panel web along a cross direction at plurality of locations between the location where the base web and fastener pieces are fixedly secured and the location where the refastenable portions releasably engage the body panel web. Preferably, the successive perforations are made prior to fixedly securing the plurality of discrete fastener pieces to the body panel web.

In another aspect, the fastener pieces each include a first and second side. In one preferred embodiment, the first side is fixedly secured to the body panel web. The second side includes the refastenable portion, which preferably faces away from the body panel web. In an alternative preferred embodiment, the first side also includes the refastenable portion, which faces, and is preferably releasably engaged with, the body panel web.

In yet another aspect, the refastenable garment includes a first and second body panel and a crotch portion extending therebetween. In one preferred embodiment, the crotch portion is folded such that the first and second body panel webs face each other. In one preferred embodiment, the first and second body panel webs are attached at a plurality of cross direction attachment locations spaced along the machine direction to form a plurality of side seams. Also in one preferred embodiment, the first and second body panel webs are cut along the cross direction at the side seams to form the discrete absorbent garments. In one preferred embodiment, the side seams are formed simultaneously with the fixed securement of the fastener pieces to the body panel web.

In another aspect, the method further comprises successively fixedly securing a plurality of discrete extension panels to the second body panel web at an attachment location and successively cutting the second body panel web and extension panels along a cross direction at the attachment location.

In yet another aspect, a refastenable absorbent garment includes a first body panel having first and second opposite side edges, a second body panel having first and second opposite side edges and a crotch portion extending between the first and second body panels. At least a first and second fastener member are secured to and extend outboard from the first and second opposite side edges of the first body panel respectively. Each of the first and second fastener members comprises a refastenable portion. A first and second extension member are secured to and extend outboard from the first and second opposite side edges of the second body panel respectively. The refastenable portion of the first fastener member releasably engages the first extension member and the refastenable portion of the second fastener member releasably engages the second extension member. In one preferred embodiment, the refastenable portion comprises a hook material.

The present invention provides significant advantages over other absorbent garments and methods and apparatus for the manufacture thereof. For example, in one embodiment of a pant-type garment, the user can pull the garment on or off like underwear. However, by making the absorbent garment refastenable, it can be applied without needing to pull the garment on or off like a pant-like garment, if desired. For example, the garment can be pulled on like a pant-type garment, and removed like a diaper-type product by disengaging the fastener members and breaking the lines of weakness. Alternatively, the garment can be pulled on and off like a pant-like garment, and can thereafter be converted to a refastenable garment, if desired. For example, the garment can be made bigger or smaller simply by adjusting the positioning of the fasteners. Moreover, in one particular application, wherein the garment is used by adults, for example with occasional incontinence problems, the garment can be pulled up or down by the user, or the fastening system may be disengaged and engaged repeatedly by the user while the garment remains unsoiled over an extended period of time.

In one preferred embodiment, the absorbent garment includes elastic elements extending along the waist region. The elastic elements provide a snug, comfortable fit that does not create a bulky appearance beneath the user's outer garments. The combination of the refastenable fasteners with the elastic elements further enhances the fit and appearance of the garment.

The process and apparatus also provide significant advantages. For example, the manufacturer can easily switch between the manufacture of a non-refastenable, pant-type product and a refastenable product simply by introducing a plurality of fastener pieces, and applying those fastener pieces to one or both of the front and rear body panels. Other modules may be added or omitted as desired. For example, a cutter may be introduced to make various cross direction cuts, for example perforations, in the front or rear body panel, and various bonders and rotators can be introduced to align and apply the fastener pieces. In this way, the machinery and equipment used to fabricate the body panels and crotch portion can be integrated into both processes, thereby maximizing the use of the assets and reducing the costs and space needed for the manufacturing facility.

In addition, the size of the absorbent garment can be easily changed, simply by increasing or decreasing the length of the fastener pieces, without changing the machine pitch of the stream of products. In particular, the distance between the side edges of the body panel(s), otherwise defined as the lateral width of the absorbent garment, can be maintained as a constant, while at the same time lengthening or shortening the fastener members such that they can accommodate larger or smaller users respectively. In this way, the process can be quickly modified to manufacture different size products without having to reconfigure various machines and apparatus. For example, the distance between the cuts made by various dies and cutters doesn't have to be altered, which greatly reduces the amount of down time when making product changes.

The present invention, together with further objects and advantages, will be best understood by reference to the following detailed description taken in conjunction with the accompanying drawings.

BRIEF DESCRIPTION OF THE DRAWINGS

FIG. 3 is plan view of an alternative embodiment of a refastenable absorbent garment in an unfastened configuration.

FIG. 4 is plan view of an alternative embodiment of a refastenable absorbent garment in an unfastened configuration.

FIG. 5 is a partial schematic top view representation of one preferred method of fabricating a portion of one embodiment of a refastenable absorbent garment.

FIG. 6 is a partial schematic top view representation of an alternative preferred method of fabricating a portion of one embodiment of a refastenable absorbent garment.

FIG. 7 is a partial schematic top view representation of an alternative preferred method of fabricating a portion of one embodiment of a refastenable absorbent garment.

FIG. 8 is a partial schematic top view representation of an alternative preferred method of fabricating a portion of one embodiment of a refastenable absorbent garment.

FIG. 9 is a partial schematic top view representation of an alternative preferred method of fabricating a portion of one embodiment of a refastenable absorbent garment.

FIG. 10 is a partial schematic top view representation of an alternative preferred method of fabricating a portion of one embodiment of a refastenable absorbent garment.

FIG. 11 is a partial schematic top view representation of an alternative preferred method of fabricating a portion of one embodiment of a refastenable absorbent garment.

FIG. 12 is a partial schematic top view representation of an alternative preferred method of fabricating a portion of one embodiment of a refastenable absorbent garment.

FIG. 13 is a partial schematic top view representation of an alternative preferred method of fabricating a portion of one embodiment of a refastenable absorbent garment.

FIG. 14 is an enlarged portion of the absorbent garment subsassembly shown in FIG. 13.

FIG. 15 is a partial schematic top view representation of an alternative preferred method of fabricating a portion of one embodiment of a refastenable absorbent garment.

FIG. 16 is a plan view of one embodiment of a body panel.

FIG. 17 is a plan view of one alternative embodiment of a body panel.

FIG. 18 is a plan view of one alternative embodiment of a body panel.

FIG. 19 is a partial schematic top view representation of an alternative preferred method of fabricating a portion of one embodiment of a refastenable absorbent garment.

FIG. 20 is a perspective view of one embodiment of a refastenable absorbent garment.

FIG. 21 is a plan view of a portion of one embodiment of a refastenable absorbent garment.

DETAILED DESCRIPTION OF THE PRESENTLY PREFERRED EMBODIMENTS

Figure 1:
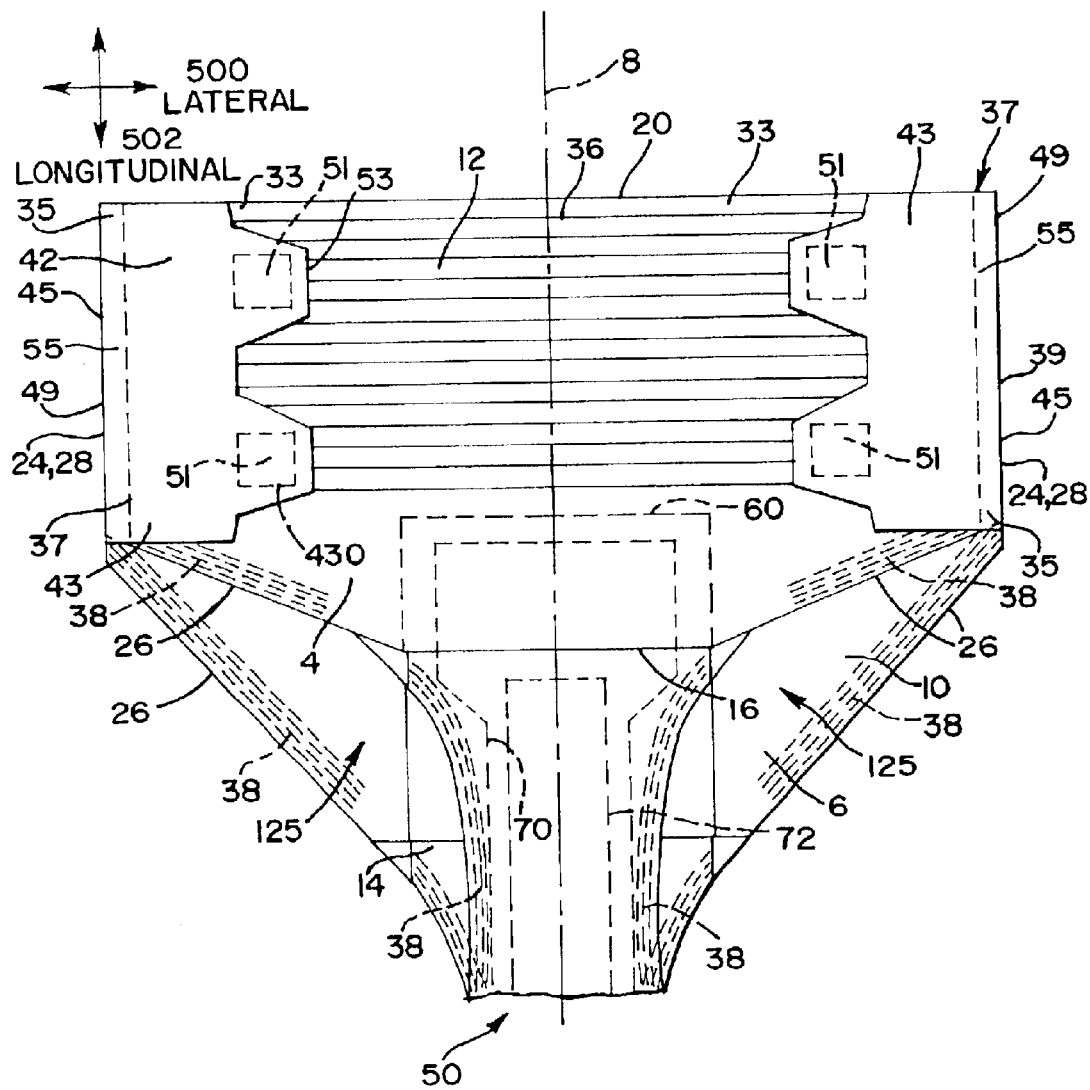
FIG. 1 is a front view of one embodiment of a refastenable absorbent garment in a fastened configuration.

Referring to FIG. 1, it should be understood that the term "longitudinal," as used herein, means of or relating to length or the lengthwise direction 502, and in particular, the direction running between the front and back of the user. The term "laterally," as used herein means situated on, directed toward or running from side to side, and in particular, a direction 500 running from the left to the right of a user, and vice versa. The terms "upper," "lower," "inner," and "outer" as used herein are intended to indicate the direction relative to the user wearing an absorbent garment over the crotch region, while the terms "inboard" and "outboard" refer to the directions relative to a centerline 8 of the garment. For example, the terms "inner" and "upper" refer to a "bodyside," which means the side closest to the body of the user, while the terms "outer" and "lower" refer to a "garment side."

The term "bodyside" should not be interpreted to mean in contact with the body of the user, but rather simply means the side that would face toward the body of the user, regardless of whether the absorbent garment is actually being worn by the user and regardless of whether there are or may be intervening layers between the component and the body of the user. Likewise, the term "garment side" should not be interpreted to mean in contact with the garments of the user, but rather simply means the side that faces away from the body of the user, and therefore toward any outer garments that may be worn by the user, regardless of whether the absorbent garment is actually being worn by a user, regardless of whether any such outer garments are actually worn and regardless of whether there may be intervening layers between the component and any outer garment.

The term "machine direction" means the direction of flow as the various members and webs progress along the fabrication line and process. It should be understood that various separate members or webs can each be traveling in a machine direction, but with the various machine directions not necessarily being parallel or oriented in the same direction. For example, one web may be traveling along a first machine direction, which is substantially perpendicular to the travel of another web in a second machine direction.

The term "cross direction" means the direction substantially perpendicular to the machine direction.

The term "downstream" means that one item is positioned more closely to the output or finished product end of the machine and/or process relative to another item. Conversely, the term "upstream" means that an item is positioned more closely to the input end of the machine or process relative to another item. For example, the output end is downstream of the input end, and vice versa, the input end is upstream of the output end.

The phrases "removeably attached," "removeably attaching," "removeably connected," "removeably engaged," "releasably attached," "releasably connected," or "releasably engaged," and variations thereof, refers to two or more elements being connected or connectable such that the elements tend to remain connected absent a separation force applied to one, both or all of the elements, and where the elements are capable of being separated upon the application of a separation force. The required separation force is typically beyond that encountered while wearing the absorbent garment.

The phrases "fixedly secured," "fixedly engaged," "fixedly attached," "fixedly connected," and variations thereof, refers to two or more elements being connected or connectable such that they are not disconnected or otherwise separated, and are not intended to be separated or disconnected, during the normal operation and use of the absorbent garment.

The term "web" refers to a continuous stream of material, whether made from one or more layers or substrates, and regardless of whether it may have noncontinuous, discrete items disposed thereon.

Figure 2:
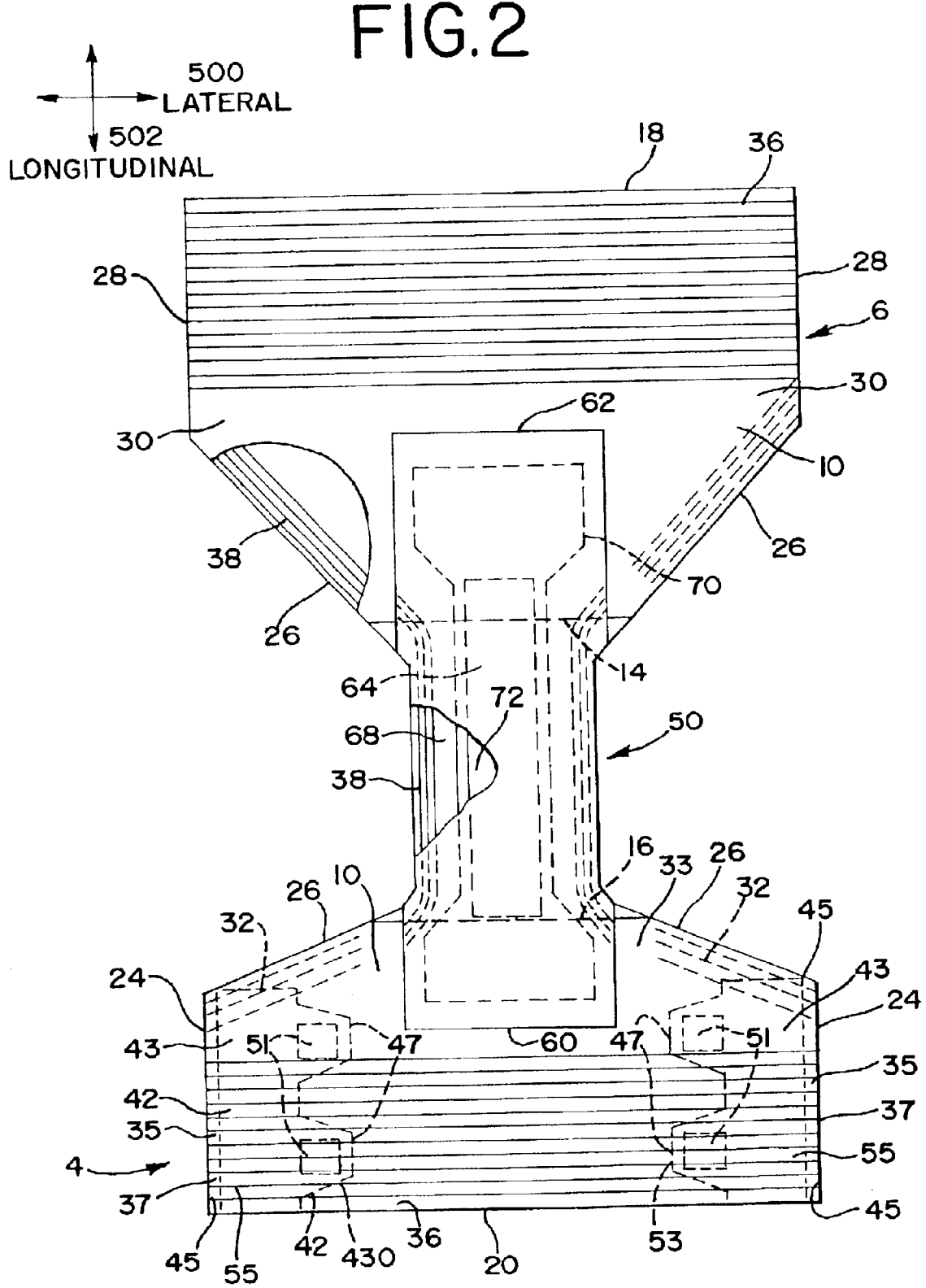
FIG. 2 is plan view of the refastenable absorbent garment shown in FIG. 1 in an unfastened configuration prior to side seams being formed.

Referring to FIGS. 1 and 2, an absorbent garment 2 includes a first, front body panel 4 and a second, rear body panel 6. The term "body panel" refers to the portion(s) of the absorbent garment, whether made of one or more layers or substrates or of one or more pieces or components, that is/are fitted circumferentially around at least the waist region of the user, including for example the user's lower back, buttock, hips and/or abdomen. The first and second body panels each have an inner, bodyside surface 10 and an outer, garment side surface 12. The first, front body panel 4 has a length, which is measured between opposed first and second terminal edges 16 and 20, and which is less than the overall length of the absorbent garment. Likewise, the second, rear body panel 6 has an overall length, which is measured between opposed first and second terminal edges 14 and 18, and which is also less than the overall length of the absorbent garment. Each of the first and second body panels has an outboard edge 24, 28 formed along the outer periphery of laterally opposed side portions of the first and second body panel. It should be understood that the outboard edges of the front and rear body panels can be different lengths.

In one preferred embodiment, each of the first and second body panels includes a tapered edge 26 on each side thereof that forms in part the leg opening, along with the side edges of the absorbent composite. The tapered edge can be straight, as shown in FIGS. 1 and 2, or curved, as shown in FIGS. 16 and 17. It should be understood that the first and second body panels can be configured without tapered side edges, such that the terminal edge of one or both of the first and second body panels extends across the entire lateral width of the body panel and forms part of the leg opening.

Referring to FIGS. 1 and 2, one or more, and preferably a plurality, meaning two or more, laterally extending elastic elements 36 are secured to each of the first and second body panels. Preferably, a plurality of laterally extending elastic elements are longitudinally spaced across substantially the entire length of a waist portion of the rear body panel 6.

In one alternative embodiment, the front body panel has a "non-elasticized" area wherein there are no laterally extending elastic elements, or other elastic or elastomeric backing members, incorporated therein or making up any portion of the thickness or cross-section of the body panel at that area, such that the material can be gathered.

Alternatively, as shown in FIGS. 1–4, the front body panel 4 can have a plurality of laterally extending elastic elements 36 spaced longitudinally along a portion thereof. The elastic elements can be spaced longitudinally along the entire length of the body panels, or along lesser lengths. For example elastic elements can extend along an upper waist portion and along the lower terminal edge defining the leg opening. It should be understood, that in an alternative embodiment, one or more separate waist bands, with or without elastic elements, can be secured to one or both of the rear and front body panels, preferably along the upper terminal edges thereof. Similarly, separate leg bands can be secured along the edges of the body panels and absorbent composite that define the leg openings. Alternatively, one or both of the body panels can be formed without any elastic elements.

In an alternative embodiment, shown in FIG. 20, the absorbent garment includes a chassis 400 having a T-shape, with a laterally extending rear body panel 402 and a crotch portion 404 extending longitudinally therefrom. An end portion 406 of the crotch portion forms a portion of a front body panel, together with a pair of fastener members 408 that are secured to the rear body panel and wrap around the user and are engaged with the end portion 406.

In another alternative embodiment, the front body panel includes a "deactivated" area wherein the elastic elements are severed, chopped or otherwise deactivated, for example by using a rotary die cutter, by melt-breaking (e.g. with a heated or ultrasonic function roll) or by any other means known to those skilled in the art. In one preferred embodiment, the deactivated area or landing zone is formed along a center portion of the front body panel and underlies a landing member and a pair of fastener members.

Referring to FIGS. 1–4, one or more leg elastic elements 38 can be secured along the inner terminal edges of the body panels 4, 6 and an absorbent composite 50 to form a gasket with the leg of the user at the leg opening 125 formed by the absorbent garment. The various waist and leg elastic elements can be formed from rubber or other elastomeric materials. One suitable material is a LYCRA® elastic material. For example, the various elastic elements can be formed of LYCRA® XA Spandex 540, 740 or 940 detex T-127 or T-128 elastics available from E.I. duPont De Nemours and Company, having an office in Wilmington, Del.

Each body panel, or chassis, is preferably formed as a composite, or laminate material, otherwise referred to as substrates or laminates, with the plurality of elastic strands sandwiched therebetween. Preferably two or more layers are bonded with various adhesives, such as hot melt, or by other techniques, including for example and without limitation ultrasonic bonding and heat pressure sealing. In one embodiment, the two layers are made of a non-woven material. It should be understood that the body panels or chassis can be made of a single layer or substrate of non-woven material, or can be comprised of more than two layers or substrates. Of course, it should be understood that other knitted or woven fabrics, elastomeric materials, non-woven fabrics, polymer films, laminates and the like can be used to form one or more of the body panel layers. The term "non-woven" web or material, as used herein, means a web having a structure of individual fibers or filaments that are interlaid, but not in an identifiable manner and without the aid of textile weaving or knitting, as in a knitted or woven fabric.

In one embodiment, the non-woven layers or substrates, and also a landing material, can be made by spunbonding. Spunbond nonwoven webs or materials are made from melt-spun filaments or spunbonded fibers which refers to small diameter fibers that are formed by extruding molten thermoplastic material as filaments from a plurality of fine, usually circular capillaries of a spinneret with the diameter of the extruded filaments then being rapidly reduced, for example, by non-eductive or eductive fluid-drawing or other well known spunbonding mechanisms. The production of spunbound nonwoven webs is described in U.S. Pat. No. 4,340,563 to Appel et al., U.S. Pat. No. 3,692,618 to Dorschner et al., U.S. Pat. No. 3,802,817 to Matsuki et al, U.S. Pat. No. 3,502,763 to Hartmann, U.S. Pat. No. 3,276,944 to Levy, U.S. Pat. No. 3,502,538 to Peterson, and U.S. Pat. No. 3,542,615 to Dodo et al, all of which are incorporated herein by reference.

The melt-spun filaments formed by the spunbond process are generally continuous and have diameters larger than 7 microns, more particularly, between about 10 and 30 microns. Another frequently used expression of fiber or filament diameter is denier, which is defined as grams per 9000 meters of a fiber or filament. The fibers may also have shapes such as those described in U.S. Pat. No. 5,277,976 to Hogle, et al, U.S. Pat. No. 5,466,410 to Hills and U.S. Pat. Nos. 5,069,970 and 5,057,368 to Largman et al., all of which are incorporated herein by reference. The spunbond filaments usually are deposited, by one or more banks, onto a moving foraminous belt or forming wire where they form a web. Spunbonded filaments generally are not tacky when they are deposited onto the collecting surface.

Spunbond fabrics typically are stabilized or consolidated (pre-bonded) in some manner immediately as they are produced in order to give the web sufficient integrity to withstand the rigors of further processing into a finished product. This stabilization (prebonding) step may be accomplished through the use of an adhesive applied to the filaments as a liquid or powder which may be heat activated, or more commonly, by compaction rolls. As used herein, the term "compaction rolls" means a set of rollers above and below the web used to compact the web as a way of treating a just produced, melt-spun filament, particularly spunbond, web, in order to give the web sufficient integrity for further processing, but not the relatively strong bonding of secondary bonding processes, such as through-air bonding, thermal bonding, ultrasonic bonding and the like. Compaction rolls slightly squeeze the web in order to increase its self-adherence and thereby its integrity.

An alternative means for performing the pre-bonding step employs a hot air knife, as described in U.S. Pat. No. 5,707,468, which is hereby incorporated herein by reference in its entirety. Briefly, the term "hot air knife" means a process of pre-bonding a just produced melt-spun filament, particularly spunbond, web, in order to impart the web with sufficient integrity, i.e., increase the stiffness of the web, for further processing. A hot air knife is a device that focuses a stream of heated air at a very high flow rate, generally from about 300 to about 3000 meters per minute (m/min.), or more particularly from about 900 to about 1500 m/min., directed at the nonwoven web immediately after its formation. The air temperature usually is in the range of the melting point of at least one of the polymers used in the web, generally between about 90° C. and about 290° C. for the thermoplastic polymers commonly used in spunbonding. The control of air temperature, velocity, pressure, volume and other factors helps avoid damage to the web while increasing its integrity.

The hot air knife's focused stream of air is arranged and directed by at least one slot of about 3 to about 25 millimeters (mm) in width, particularly about 9.4 mm, serving as the exit for the heated air towards the web, with the slot running in a substantially cross-machine direction over substantially the entire width of the web. In other embodiments, there may be a plurality of slots arranged next to each other or separated by a slight gap. The at least one slot usually, but not necessarily, is continuous, and may be comprised of, for example, closely spaced holes. The hot air knife has a plenum to distribute and contain the heated air prior to its exiting the slot. The plenum pressure of the hot air knife usually is between about 2 to about 22 mmHg, and the hot air knife is positioned between about 6.35 mm and about 254 mm, and more particularly from about 19.05 to about 76.20 mm above the forming surface. In a particular embodiment, the hot air knife plenum's cross-sectional area for cross-directional flow (i.e., the plenum cross-sectional area in the machine direction) is at least twice the total slot exit area.

Since the foraminous wire onto which the spunbond polymer is formed generally moves at a high rate of speed, the time of exposure of any particular part of the web to the air discharge from the hot air knife typically is less than a tenth of a second and generally about one hundredth of a second, in contrast with the through-air bonding process, which has a much longer dwell time. The hot air knife process has a great range of variability and control over many factors, including air temperature, velocity, pressure, and volume, slot or hole arrangement, density and size, and the distance separating the hot air knife plenum and the web.

The spunbond process also can be used to form bicomponent spunbond nonwoven webs as, for example, from side-by-side (or sheath/core) linear low density polyethylene/polypropylene spunbond bicomponent filaments. A suitable process for forming such bicomponent spunbond nonwoven webs is described in U.S. Pat. No. 5,418,045 to Pike et al., which is incorporated herein by reference in its entirety.

Commercially available thermoplastic polymeric materials can be advantageously employed in making the fibers or filaments from which pattern-unbonded nonwoven material is formed. As used herein, the term "polymer" shall include, but is not limited to, homopolymers, copolymers, such as, for example, block, graft, random and alternating copolymers, terpolymers, etc., and blends and modifications thereof. Moreover, unless otherwise specially limited, the term "polymer" shall include all possible geometrical configurations of the material, including, without limitation, isotactic, syndiotactic and random symmetries. As used herein, the terms "thermoplastic polymer" or "thermoplastic polymeric material" refer to a long-chain polymer that softens when exposed to heat and returns to its original state when cooled to ambient temperature. Preferably, the spunbond fibers are made of a polypropylene. Other alternative thermoplastic materials include, without limitation, poly(vinyl chloride)s, polyesters, polyamides, polyfluorocarbons, polyolefins, polyurethanes, polystyrenes, polyethylenes, poly(vinyl alcohol)s, caprolactams, and copolymers of the foregoing. The fibers or filaments used in making the nonwoven material may have any suitable morphology and may include hollow or solid, straight or crimped, single component, bicomponent or multicomponent, biconstituent or multiconstituent fibers or filaments, and blends or mixes of such fibers and/or filaments, as are well known in the art.

After the nonwoven web is formed, the pre-bonded or unbonded web is passed through a suitable process or apparatus, including for example a calendar roll, to form a pattern of discrete bonded areas. The term "discrete" as used herein means individual or disconnected, and is contrasted with the term "continuous" as used in U.S. Pat. No. 5,858,515 to Stokes et al, which is hereby incorporated herein by reference, and which describes pattern-unbonded, or point un-bonded nonwoven fabrics having continuous bonded areas defining a plurality of discrete unbonded areas. In one embodiment, the calendar stack (not shown) includes an anvil roll and a pattern roll, which is heated and includes various raised landing portions. The raised portions of the pattern roll thermally bond the fibers to form the bonded areas. The bonds can made of any shape and size. Preferably, the percent bonded area of the web is between about 5% and 25% of the area of the web, and is more preferably between about 10% and 15%. Thereafter, the bonded substrate can be bonded to another substrate with the elastic members disposed therebetween.

In one alternative preferred embodiment, the landing material is made of the point-unbonded nonwoven material, for example, a 2.0 osy point-unbonded material. One exemplary material of this type has been used in a HUGGIES® Ultratrim Disposable Diaper, which is commercially available from Kimberly-Clark Corporation. In another preferred embodiment, the landing material, which can be comprised of a portion of one of the body panel substrates, e.g., a body panel liner, is made of a non-woven spunbond material, for example, a spunbond material having a basis weight of preferably about 0.6 osy. In other preferred embodiments, the basis weight of each substrate can be between at least about 0.3 and about 2.0 osy, and preferably between about 0.5 osy and about 1.5 osy, and more preferably between about 0.5 osy and about 1.0 osy. Even with a relatively low percent area bonding, the relatively low basis weight nonwoven spunbond material exhibits strength and tear characteristics allowing it to be used as a body panel. Other materials that may be used as the non-woven material include various meltblown materials, and also bonded-carded materials.

In other alternative embodiments, the landing material can be made of a loop material, which typically includes a backing structure and a plurality of loop members extending upwardly therefrom. The loop material can be formed by any suitable material, such as acrylic, nylon or polyester, and can be formed from such methods as warp knitting, stitch bonding or needle punching. Suitable loop materials are available from Guilford Mills, Inc., Greensboro, N.C., U.S.A. under the trade designation No. 36549.

The body panel 4, 6 non-woven material is preferably substantially hydrophobic, which may optionally be treated with a surfactant or otherwise process to impart a desired level of wettability and hydrophilicity. In one particular embodiment of the invention, the body panel is a nonwoven, wire-weave spunbond polypropylene fabric composed of about 1.6 denier fibers formed into a web having a basis weight of about 0.6 osy. One suitable non-woven material is the Corinth 0.60 osy, 1.6 dpf wireweave, nonwettable Metallocene (EXXON ACHIEVE 2854 PP) spunbond material manufactured by Kimberly-Clark Corporation, the assignee of the present application.

Referring to FIGS. 1 and 2, fastening members 42 are preferably attached to the front body panel and extend laterally inboard relative to the outboard side edge 24 of the front body panel 4 from an attachment location 45, which is preferably located at the side edge, but which can be spaced inboard from the side edge. In the embodiment shown in FIG. 1, the front body panel 4 includes a middle portion 33, which can have a landing member secured thereto, and opposite side portions 35. Opposite longitudinally extending lines of weakness 37 separate the middle portion 33, which can include a landing member attached thereto, from the opposite side portions 35, such that the side portions 35 are initially breakably attached to opposite sides of the middle portion 33. The lines of weakness 37 can comprise a perforation or other series of cuts, a thinning, breakage or separation of material, or a strip of a different kind of material bridging between the middle portion and the side portions that is more easily torn or broken than the material of the middle portion and side portions, and which allow a user or the manufacturer to separate the side portions from the middle portion. For example, the absorbent garment can be broken after the garment is applied to a user, or beforehand. Preferably, the fastening members 42 are secured to the garment-side surface 12 of the side portions 35, preferably in a portion of a deactivacted area or zone, between the side edge 24 of the front body panel and the line of weakness 37. The elastic elements in the side portions that are not deactivated allow the side portions to be stretched to provide a snug fit around the user. It should be understood that none of the elastic elements need be deactivated. In other embodiments, the front body panel, including the side portions, may not incorporate any elastic elements, or may incorporate a limited number spaced across various portions of the length thereof, as explained herein.

Referring to the embodiments illustrated in FIGS. 3 and 20, the fastening members 42, 408 are secured to the rear body panel 6, 402 and releasably engage the front body panel 4, or the end portion 406. In an alternative embodiment, the fastener members can be secured to the front body panel and engage the rear body panel. In the embodiments of FIGS. 3, 4 and 20, the side edges 24, 28 of the front and rear body panels, or the side edges 410 of the body panel 402 and the end portion 406, are not fixedly secured to one another to form a side seam, such that the product remains "open," and is not initially pulled on like a pant-type product, unless the fastener members are first joined with the opposite body panel to form and define the leg openings. Preferably, in such an embodiment, there are no lines of weakness.

In another alternative embodiment, the fastening members can be secured to the rear body panel and can include a portion crossing over a line of weakness formed along the front body panel, or alternatively along the rear body panel, and can refastenably engage a portion of one or both of the front and rear body panels on the other side of the line of weakness. In one embodiment, the fastening members engage the body panel along at least a portion that is not elasticized. It should be understood that the line of weakness could be formed at the side seam separating the front and rear body panels. Preferably, the fastening members are fixedly secured to the outer, garment-side surface of the front and/or rear body panels, and releasably engage the outer, garment-side surface of the front and/or rear body panels, although it should be understood that the fastening members could be fixedly secured to an inner, body-side surface of front and/or rear body panels and releasably engage an inner, body-side surface of the front and/or rear body panels. For example, in FIGS. 3, 4 and 13–18, the fastener members 42 are fixedly secured to an inner, bodyside surface of the rear body panel web, which is cut to form the rear body panels.

Referring to the embodiments of FIGS. 1–3, the middle portion 33 does not include a separate landing member secured thereto. Instead, the front body panel itself serves as a landing material. Again, opposite longitudinally extending lines of weakness 37 separate the middle portion 33 from the opposite side portions 35, such that the side portions 35 are initially breakably attached to opposite sides of the middle portion 33. Preferably, the fastening members 42 are secured to the garment-side surface of the side portions 35 between the side edge 24 of the front body panel and the line of weakness 37.

In an alternative embodiment, shown in FIG. 4, the fastening members 42 are secured to the rear body panel 6, preferably a body side surface 10 thereof, and releasably engage a pair of extension members 414 or panels fixedly secured to the side edges 24 of the front body panel 4. The extension panels have a curved, outboard edge 416 and are preferably made of one or more of the above-referenced body panel materials. It should be understood that the extension panels can be made of a landing material, including for example a loop material, or may include a landing member secured thereto for engagement with the fastener members 42 secured to the rear body panel. The extension members can also be elasticized, for example by way of incorporation of elastic elements across various portions thereof.

Referring to the embodiments of FIGS. 1 and 2, the opposite side edges 24 of the front body panel 4 are joined to the opposite side edges 28 of the rear body panel 6 to form a seam 39. The seam 39 is formed by bonding, sewing or otherwise attaching the side edges. For example, in one preferred embodiment, the side seams are formed by ultrasonic bonds. In this way, prior to the breaking of the line of weakness 37, the absorbent garment can be configured as a pant-like garment, which can be pulled over the legs of the user. After the garment is applied to the user, the lines of weakness can be broken, if desired, or left intact, as the fasteners are adjusted to fit the garment to the user. If desired, the lines of weakness can be broken prior to securing the garment to the user, for example when the user is bed-ridden. In this configuration, the garment is laid beneath the user and is secured to the user with the fastening tabs. By providing the side portions, and by connecting the fastening tabs to the front body panel, instead of the rear body panel, the tabs are located at the front of the user so as to not provide discomfort to the user when lying on their backs and to allow the fasteners to be more easily seen and adjusted by the user or caretaker.

It should be understood that the lines of weaknesses and the fasteners can be moved laterally inboard and outboard to provide more or less adjustment capability. In addition, the elasticized side portions or fastener members can provide further adjustment capability.

In the embodiments shown in FIGS. 3, 4, 13 and 20, the lines of weakness are omitted altogether, and the side edges 24, 28, 410 of the front and/or rear body panels are not fixedly joined to form a side seam. Instead, the fastener members fixedly secured to one of the front and rear body panels releasably engage the other of the front and rear body panels to thereby join the front and rear body panels and define the leg openings for the user.

It should be understood that the front and rear body panels can be made as an integral unitary member that extends along the crotch from the front to back and with the sides thereof connected to form side seams. Alternatively, the front and rear body panels can be formed integrally as a ring-like member, for example as one body panel extending around the waist and hips of the user, that is attached to a crotch portion that forms leg openings.

In one alternative embodiment, an outer cover is disposed over the entire garment and forms the outer garment side layer or substrate of the front and rear body panels, with the various elastic elements 36, 38 disposed between a bodyside liner on each of the front and rear body panels, which liner preferably is configured as a single substrate, and the outer cover, which is also preferably configured as single substrate. In this way, the portion of the outer cover that overlies the front body panel liner and is fitted around the front of the user forms part of the front body panel, while the portion of the outer cover that overlies the rear body panel liner and is fitted around the rear of the user forms part of the rear body panel. The front and rear body panels, with the liners and with the outer cover forming portions thereof and preferably extending therebetween, forms a chassis. The outer cover is preferably made of a non-woven material, similar to that of the other body panel materials described herein. It should be understood that the body panels, including the outer cover, can be configured with any number of a plurality of substrates, and that the body panels can include other layers and substrates.

Preferably, as shown in FIGS. 1–4, the fastening members 42 comprise a carrier member 43 that is formed in a generally side-ways, "U" shape, with a vertical extending base member 55 and a pair of laterally extending and longitudinally spaced tab members 47. The tabs can have curved edges, or can be linear. The carrier member can also include a single tab member, or more than two tab members.

Alternatively, as shown in FIGS. 7, 8 and 10–12, the carrier member 424 has a square or rectangular shape, with straight side edges 422. In one embodiment, a refastenable material can extend beyond the edges of the carrier member to form tabs. In the embodiment shown in FIG. 12, a laterally extending slit 423 is formed in the carrier member 424. The slit 423 extends laterally inboard from a free edge of the carrier member. The slit 423 forms a pair of tab members on each fastener member. It should be understood that additional slits can be formed in the carrier member to thereby define additional tab members.

As shown in FIGS. 1–2, the carrier members are preferably fixedly secured to the side portions of the front body panel 4 with adhesive bonds 49, sonic bonds, thermal bonds, pinning, stitching or other known types of attachment. In alternative embodiments, the fastening members 42 can be fixedly secured to the rear body panel 6, as shown in FIGS. 3 and 4, or to one or both of the front and rear body panels, e.g., at the seam.

In a preferred embodiment, the pair of fastener members 42 used to releasably secure the front and rear body panels define a "fastening system," which refers to the grouping of fastener members used to releasably secure two or more portions of an absorbent garment. Although the fastening system is shown as being configured with two fastener members, it should be understood that it could include additional fastener members, and that the two-fastener member fastening system shown in the Figures is meant to be illustrative rather than limiting. For example, the fastening system could include three, four or even more fastener members.

The tab members 47 are preferably oriented toward each other on either of the front and rear body panels when in use, although it should be understood that they can extend away from each other. Referring to FIGS. 3 and 4, one of the fastener members 42 is shown as being folded down over and releasably engaged with the body side surface of the rear body panel, which is the configuration of the fastener members when packaged. The other fastener member 42 is shown as being disengaged from the rear body panel in an unfolded configuration wherein it is ready for releasable engagement with the front body panel 4, or landing member secured thereto. In such an embodiment, the fastener member 42 and tab members 47 are rotated about the attachment location 45 so that they can engage the front body panel.

Each carrier member 43 has a longitudinal length and each of the tab members 47 comprises a refastenable portion or an engagement portion having a longitudinal length. The refastenable portion 51 preferably comprises an array of hooks, as explained below, but alternatively can comprise various adhesives, such as pressure sensitive adhesives, buttons, zippers, snaps and other releasable and reattachable fastening devices known to those skilled in the art. Referring to the embodiment of FIG. 3, the refastenable portion 51 extends along the entire length of the tab members. Alternatively, as shown in FIGS. 1, 2, 4, 11 and 12, the refastenable portion is configured as a patch member 430 secured to the carrier member. Alternatively, as shown in FIGS. 9 and 10, the refastenable portion, preferably configured as a strip 420, extends laterally beyond and outboard of the side edges 422 of the carrier member 424. As shown for example in FIG. 20, the carrier member 424 can include various laterally extending elastic elements 36 spaced longitudinally therealong to provide the fastener member with various elastic properties such that it can be extended to provide additional adjustment capabilities. The elastic elements can be deactivated beneath the refastenable portion if desired.

In yet another alternative embodiment, shown in FIGS. 19 and 20, the refastenable member 432, or portion, extends longitudinally along substantially the entire length of the carrier member 424, although it should be understood that the refastenable portion can be configured as one or more separate discrete patch members, or can extend along the entire length of the carrier member, or some lesser length thereof.

In the embodiment shown in FIGS. 1–3, each fastening member 42 is comprised of two separate, longitudinally spaced tab members 47. In any of the embodiments, the two or more tab members provides a pant-like fit that controls the waist and leg openings in the front and back of the garment, and also allows the user to adjust the fit of the garment without totally undoing the garment. For example, the user can release one of the tab members and refasten it without undoing the other tab member.

In an alternative embodiment, shown in FIG. 9, a pair of fastener members are secured to each side of the body panel. The fastener members are preferably configured as a laterally extending strip 420 of refastenable material. The pair of strips 420 on each side of the body panel again provide the user with the ability to adjust the fit of the garment without undoing one or both sides thereof. The strips can be secured directly to the body panel, or alternatively the strips 420 can be secured to a carrier member 424, as shown in FIG. 10. It should be understood that a single strip, or more than two strips, with or without a carrier member, can be secured to the front or rear body panels.

It should be understood that any of the various fastener member configurations, and refastenable configurations, described herein can be used interchangeably.

In the embodiment of FIGS. 1–13 and 20, the fastener member 42, 408, whether configured with a carrier member and a refastenable portion or with a refastenable member alone, has a first side 440 and a second side 442, as shown in FIGS. 3 and 4. Preferably, the first side of the fastener member is fixedly secured to either the garment side surface 12 of the front body panel or the body side surface 10 of the rear body panel. In addition, the first side 440 further includes the refastenable portion, which faces and is releasably engaged with either the bodyside surface 10 of the rear body panel, when the fastener member is in the folded, packaged configuration prior to use, or with the garment side surface 12 of the front body panel 4 when in use.

Alternatively, as shown in the embodiments of FIGS. 13–18 and 21, the fastener member 420 does not include any carrier member, but rather has a first side fixedly attached to the body side surface 10 of the rear body panel and a second side, which is configured as the refastenable portion and which faces away from the body side surface. As shown in the embodiments of FIGS. 16–18, one, two or three fastener members 420 are secured to the rear body panel, although it should be understood that additional fastener members, or other configurations thereof, could be used. As shown in FIG. 21, the fastener member 420 is elongated along the longitudinal direction, and, in one embodiment, can extend substantially the entire length of the waist portion of the rear body panel. In addition, it should be understood that the fastener member could include a carrier member having a first side secured to the garment side surface of the body panel and a second side supporting the refastenable portion, which faces away therefrom.

In one preferred embodiment, the refastenable portion 51 comprises a hook-type fastener member, or hook strip, which is secured to the carrier member 43, 424 with adhesive, ultrasonic bonding, stitching or other known attachment devices. In one embodiment, shown for example in FIG. 3, the end portion 53 or tip of the carrier member can be left uncovered by the refastenable portion 51, such that it can be lifted or flexed and grasped by a user as they disengage or peel back the fastener member. In another embodiment, shown in FIGS. 9 and 13–18, the entire fastener member 420 is configured as a hook strip, with the hooks arranged on the first side of the strip and facing away from the second side of the strip. In one embodiment, the hooks can be deadened along a portion of the first side of the strip in the attachment location, such that the first side can be fixedly secured to the body panel.

It should be understood that the term "hook" as used herein means any element capable of engaging another element, and is not intended to limit the form of the engaging elements, for example to include only "hooks," but rather encompasses any form or shape of engaging element, whether unidirectional or bi-directional. Various hook configurations are described in U.S. Pat. No. 5,845,375 to Miller et al., U.S. Pat. No. 6,132,660 to Kampfer, U.S. Pat. No. 6,000,106 to Kampfer, U.S. Pat. No. 5,868,987 to Kampfer, U.S. Pat. No. 4,894,060 to Nestegard, and U.S. Pat. No. 6,190,594 B1 to Gorman, the entire disclosures of which are incorporated by reference herein. Some examples of hook fasteners are the various CS600 hook fasteners, including the XKH-01-002 CS600, 2300 Pin Density hook fastener (Part No. XKH-01-002/60MM/SP#2628), manufactured by Minnesota Mining and Manufacturing Co., St. Paul Minn. Another example of a hook fastener are the Velcro® HTH-851 and HTH-829 hook fasteners available from Velcro USA, Inc.

In one preferred embodiment, a mushroom-type hook strip comprises a homogeneous backing of thermoplastic resin and, integral with backing, an array of upstanding stems distributed across at least one face of the backing, each having a mushroom head. The array of hooks on each strip comprise an engagement portion having a longitudinal length. The stems can have a molecular orientation as evidenced by a birefringence value of at least 0.001, and the mushroom heads having circular disc shapes with generally planar end surfaces opposite the backing, which disc shaped heads preferably have diameter to thickness ratios of greater than about 1.5 to 1.

The stems of the hook strip can be molecularly orientated as evidenced by a birefringence value of at least 0.001. As such, they have significantly greater stiffness and durability, as well as greater tensile and flexural strength, than would be achievable without such orientation. Because of these qualities, the portions of the stems not heated by a heating surface during the forming process remain resiliently flexible during a deforming step, which preferably involves the application of heat to the stem tips by contact with the heated surface of a metal roller. Such contact forms the tip of each stem into a circular disc shaped mushroom head at the tip of each stem, which head has a substantially flat inner surface that enhances its holding power when engaged with a loop.

As compared to hook strips that have unoriented stems, the enhanced strength of the hooks of the hook strip makes them less likely to break during disengagement. When the hook strip is used with the non-woven material herein described, the enhanced strength of the hooks makes them less likely to break under disengagement forces than the fibers of the material, a beneficial attribute for at least two reasons. First, broken hooks can create debris whereas a broken fiber typically does not. Furthermore, the non-woven material typically contains many more engageable fibers than there are hooks per unit area, thus allowing a greater number of disengagements before a hook-and-loop fastener becomes useless.

Although the stems of the hook strip preferably are generally circular in cross section, other suitable cross sections include rectangular and hexagonal. The stems preferably have fillets at their bases, both to enhance strength and stiffness and for easy release from a mold in which they are formed. In addition, the stems can be tapered, preferably from a larger to a smaller cross-section as one moves from the base to the head.

The stem portions are preferably at an angle of about 90 degrees from the backing substrate, however, this angle can range from about 80 to about 100 degrees, preferably 85 to about 95 degrees. The hook head portion is formed on the distal end of the stem. The hook head can be elongated in on or more directions forming the fiber engaging portions. These fiber engaging portions extend outward from the stem portion at any angle so that they can project upwardly away from the film backing, parallel with the film backing or even downward toward the film backing.

For example, the hook head portion has a deformed fiber engaging portion that projects downward. Preferably, the lower surface of the fiber engaging portion also projects downward form a crook between the lower face of the fiber engaging portion and the stem base portion. In one preferred embodiment, the heads of the hooks generally project at a downward angle from the hook head top portions toward the base. This downward angle (measured from a reference line taken from the top of the hook head and parallel with the backing) is generally from about 0 to about 70 degrees, preferably from about 5 to about 60 degrees and most preferably from about 5 to about 35 degrees (defined by a linear extent running from a center region of the hook head top portion to an end of the hook head fiber engaging portion).

The head shape with its high diameter to thickness ratio, and the small size and close spacing or high density of individual hooks that are provided by the hook strip according to the present invention makes it able to easily firmly releasably engage non-woven materials in shear, possibly because the many thin heads can easily move radially into engagement with rather small fibers. Thus the hook strip is particularly useful for hook-and-loop fastening when the "loops" are provided by non-woven materials which are not particularly adapted for use as the loop portions of hook and loop fasteners, and which are not as well engaged by known prior art hook strips. For example, the hook strip is particularly well-suited for engaging the topographically flatter non-woven materials described above, including the non-woven spunbond material, which has relatively fewer loose, outwardly extending, free fibers than conventional loop materials, but still provides a relatively high number of pores, of sufficient size, such that the material can be engaged by the hooks. Indeed, once the hooks are received in the pores, or embedded in the non-woven material, the fastening tabs provide excellent shear characteristics, such that the garment is securely fastened during normal wearing conditions.

In general, the hooks are of uniform height, preferably of from about 0.10 to 1.30 mm in height, and more preferably from about 0.18 to 0.51 mm in height; have a density on the backing preferably of from 60 to 1,600 hooks per square centimeter, and more preferably from 125 to 690 hooks per square centimeter, and preferably greater than about 150 hooks per square centimeter; have a stem diameter adjacent the heads of the hooks preferably of from 0.07 to 0.7 mm, and more preferably from about 0.1 to 0.3 mm. The deformed hook heads project radially past the stems on at least one side preferably by an average of about 0.01 to 0.3 mm, and more preferably by an average of about 0.02 to 0.25 mm and have average thicknesses between their outer and inner surfaces (i.e., measured in a direction parallel to the axis of the stems) preferably of from about 0.01 to 0.3 mm and more preferably of from about 0.02 mm to 0.1 mm. The hook heads have average head diameter (i.e., measured radially of the axis of the heads and stems) to average head thickness ratio preferably of from 1.5:1 to 12:1, and more preferably from 2.5:1 to 6:1.

For most hook-and-loop uses, the hooks of the hook strip should be distributed substantially uniformly over the entire area of the hook strip, usually in a square or hexagonal array.

To have both good flexibility and strength, the backing of the hook strip preferably is from 0.02 to 0.5 mm thick, and more preferably is from 0.06 to 0.3 mm in thick, especially when the hook strip is made of polypropylene or a copolymer of polypropylene and polyethylene. For some uses, a stiffer backing could be used, or the backing can be coated with a layer of pressure sensitive adhesive on its surfaces opposite the hooks by which the backing could be adhered to a substrate, such as the carrier member 43, so that the backing could then rely on the strength of the substrate to help anchor the hooks.

Virtually any orientable thermoplastic resin that is suitable for extrusion molding may be used to produce the hook strip. Thermoplastic resins that can be extrusion molded and should be useful include polyesters such as poly(ethylene terephthalate), polyamides such as nylon, poly(styrene-acrylonitrile), poly(acrylonitrile-butadiene-styrene), polyolefins such as polypropylene, and plasticized polyvinyl chloride. One preferred thermoplastic resin is a random copolymer of polypropylene and polyethylene containing 17.5% polyethylene and having a melt flow index of 30, that is available as SRD7-463 from Shell Oil Company, Houston, Tex.

The hook strip has preferably substantially continuous planar backing of thermoplastic resin. Integral with the backing is the array of hooks projecting generally at right angles to one major surface of the backing. Each of the hooks has a stem, and, at the end of the stem opposite the backing, a generally circular plate-like cap or head projecting radially past or overhanging the stem so as to form a fiber engaging portion that projects downward. Preferably, the lower surface of the fiber engaging portion also projects downward form a crook between the lower face of the fiber engaging portion and the stem base portion. The stem can also have a fillet around its base.

When the absorbent garment is secured to the user, the fastening members 42, 408 secured to the side portions of the front body panels 4 or rear body panels 6, or elsewhere as described above, releasably engage or are otherwise connected to the front body panel, or a landing member secured thereto. In particular, the heads on the hooks engage the fibers of the front body panel, or of the landing material. In particular, the heads on the hooks engage the fibers of the body panel, whether elasticized or not, or alternatively the landing material making up the landing member. The refastenable portions 51 can be initially engaged with the fibers to form a mechanical bond with the body panel or landing member during the manufacturing process so as to help maintain the connection between the side and middle portions. In the embodiments of FIGS. 3, 4 and 20, where the absorbent garment is preferably sold to the user as an "open product," the refastenable portions 51, 432 are initially engaged with body side surface 10 of the rear body panel, preferably with a mechanical bond, during the manufacturing process so as to maintain the fastener member flat against the body panel such that it does not interfere with the folding and packaging process. When the user desires to put on the absorbent garment, the fastener members 42, 408 are peeled back so as to disengage the refastenable portion 51, 432 from the rear body panel, preferably the body side surface thereof. The fastener members 42, 408 are rotated about the attachment location 45, wherein the tab members 47 extend laterally outward and preferably outboard from the side edges 28. The user then reapplies the refastenable portion 51, 432 to the front body panel so as to releasably secure the front and rear body panels to one another about the user.

Referring to FIGS. 1–12 and 19–21, the absorbent garment includes an absorbent composite 50 having first and second longitudinally opposed terminal end edges 60, 62. Referring to FIGS. 2–4, the absorbent composite preferably includes a substantially liquid permeable topsheet 64, or liner, and a substantially liquid impermeable backsheet 68, or outer cover. A retention portion 70 is disposed or sandwiched between the topsheet and the backsheet, which are connected. The topsheet, backsheet and other components of the absorbent composite 50 can be joined for example with adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein. It should be understood that the term "absorbent composite" refers to any material or assembly capable of absorbing liquids or bodily exudates, and may be comprised of a single material or component, for example a retention portion.

Additional layers, including for example, a surge layer 72, are also preferably incorporated into the absorbent composite. Preferably, the surge layer does not run the entire length of the absorbent composite and is shorter than the retention portion. The topsheet can be indirectly joined to the backsheet by affixing the topsheet to intermediate layers, such as the surge layer or retention portion, which in turn is affixed to the backsheet. The absorbent composite can further include one or more longitudinally extending barrier cuffs formed along the opposite lateral sides of the absorbent composite on the body side surface thereof.

The backsheet 68 is preferably liquid impermeable, but may be liquid permeable, e.g., when an additional barrier layer is used with the retention portion. For example, in one embodiment, the backsheet can be made from a thin plastic film, or other flexible, substantially liquid-impermeable material. As used herein, the term "flexible" means a material that is compliant and which will readily conform to the general shape and contour of the body of the user. The backsheet prevents various bodily fluids and exudates from wetting or otherwise contaminating various bedding or outer garments worn by the user over the absorbent garment. In particular, the backsheet can include a film, such as a polyethylene film, having a thickness of from about 0.012 mm to about 0.051 mm.

In various constructions, the topsheet can comprise various woven or nonwoven materials. For example, the topsheet can be composed of a meltblown or spunbonded web of desired fibers, and may also be a bonded-carded web. For example, the topsheet can be made of a substantially hydrophobic material, and the hydrophobic material may optionally be treated with a surfactant or otherwise processed to import a desired level of wettability and hydrophilicity. In one particular embodiment of the invention, the topsheet is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

In various constructions, the backsheet can comprise a woven or nonwoven fibrous web layer, which is treated or constructed, partially or wholly, to impart the desired levels of liquid impermeability to selected regions that are adjacent to or proximate the absorbent retention portion. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers). A material of this type has been employed to form the outercover of a HUGGIES® Ultratrim Disposable Diaper, which has been commercially available from Kimberly-Clark Corporation. The backsheet can provide the outercover of the article, particularly in the crotch region. Optionally, however, the article may include a separate outercover component member, as disclosed herein, which is additional to the backsheet. The outercover can be joined, for example, to one or more of the absorbent composite and/or body panels as explained above.

The backsheet may include a micro-porous, "breathable" material which permits gases, such as water vapor, to escape from the absorbent garment while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In various configurations of the invention, where a component, such as the backsheet is configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 Method 5514, 1978, or an equivalent thereof.

In one preferred embodiment, the backsheet is sufficiently impermeable to liquid and semi-liquid materials to substantially prevent the undesired leakage of waste materials, defined as exudates, including for example urine and feces. For example, the backsheet member can desirably support a hydrohead of at least about 45 centimeters (cm) substantially without leakage. The backsheet member can alternatively support a hydrohead of at least about 55 cm, and optionally, can support a hydrohead of at least about 60 cm, or more, to provide improved benefits.

The backsheet and/or outercover also can be extensible. In one preferred embodiment, the backsheet and/or outercover is capable of providing an elongation of at least about 1 cm when subjected to a tensile force of 11.8 g/cm, and further provides a substantially permanent deformation of at least about 20% when subjected to a tensile force of 19.70 g/cm and is then allowed to relax under a zero applied stress for a period of 1 minute.

For example, the extensible member can be composed of a necked fiber, a creped fiber, a micro-pleated fiber, polymer films or the like, as well as combinations thereof. The fabrics may be woven or nonwoven materials, such as spunbond fabrics. One example of a suitable extensible material is a 60% necked, polypropylene spunbond having a basis weight of about 1.2 osy.

The backsheet and/or outercover also can be expandable, for example when it has one or more folds, e.g., one or more z-folds (not shown), or can be both extensible and expandable. The term expandable as used herein means to enlarge or to increase the extent or area, lateral and/or longitudinal, thereof, e.g., by unfolding one or more folds.

The retention portion 70 is preferably made of an absorbent material, which can be any material that tends to swell or expand as it absorbs exudates, including various liquids and/or fluids excreted or exuded by the user. For example, the absorbent material can be made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material. Various acceptable absorbent materials are disclosed in U.S. Pat. Nos. 5,147,343 for Absorbent Products Containing Hydrogels With Ability To Swell Against Pressure, 5,601,542 for Absorbent Composite, and 5,651,862 for Wet Formed Absorbent Composite, all of which are hereby incorporated herein by reference. Furthermore, the proportion of high-absorbency particles can range from about 0 to about 100%, and the proportion of fibrous material from about 0 to about 100%. Additionally, high absorbency fibers can be used such as Oasis type 121 and type 122 superabsorbent fibers available from Technical Absorbent Ltd., Grimsby, Lincolnshire, United Kingdom.

The retention portion 70 has laterally opposed side edges 74 and preferably can be made of a single or dual layer of absorbent material. The retention portion preferably has an hour-glass shape with enlarged end regions. Alternatively, the retention portion can include a folded or multi-layered configuration. The retention portion preferably has a length substantially equal to, or slightly shorter than, the length of the absorbent composite. The retention portion can include one or more barrier layers attached to the absorbent material. In one embodiment, an upper tissue substrate is disposed adjacent the retention portion. Alternatively, a lower tissue substrate can be disposed adjacent an opposite side of the retention portion, or the tissue can completely envelope the retention position.

Referring to FIGS. 1–4, the opposite garment side of the end regions of the absorbent composite, and in particular, the outer, garment side surface of the backsheet 68, are secured to the bodyside surface of the longitudinally opposed crotch ends of the first and second body panels 4, 6, and in particular the liner portion of those body panels. Likewise, and referring to FIG. 20, the absorbent composite is secured to the bodyside surface of the chassis 400. It should be understood that the absorbent composite can be secured using any of the methods of attachment described above, including for example various adhesives, stitching or other bonding methods. The absorbent composite can be secured to the body panels with any configuration of attachment lines, swirls, patterns, spots, etc., or can be a full and continuous attachment therebetween. In addition, it should be understood that the absorbent composite can be attached to the garment side surface of the body panels.

Referring to FIGS. 5–12, 13–15 and 19, various preferred methods for fabricating one or more embodiments of the aforedescribed refastenable absorbent garments are illustrated. Although the processes are described in terms of various zones, it should be understood that they are continuous processes.

Referring to FIGS. 5–12, a continuous first body panel web 120, which preferably forms the front body panel, and which is preferably made of one or more of the materials described above, is moved along in the process in a machine direction. The front body panel web 120 is further secured to the absorbent composite 50, which is also secured to a continuous rear body panel web 148 that forms the rear body panel. In particular, the front body panel web 120 moves along a path parallel to the rear body panel web 148 in the machine direction. The absorbent composite 50, extending in the cross direction, is then applied to the bodyside of each of the front and rear body panel base webs 120, 148 to form a ladder type configuration, although it should be understood that the absorbent composite could be attached to the garment side of each body panel. The absorbent composite 50 can be assembled in a machine direction and can thereafter be rotated and applied to the front and rear body panel base webs. The absorbent composite can be incorporated either before or after the assembly of the front and rear body panel webs. In one preferred embodiment, where the outer cover is secured to and forms part of the front and rear body panels and a crotch portion 462 of the absorbent garment, the absorbent composite 50 is applied to the body chassis after the outer cover and body panel liners are joined with the elastic elements disposed therebetween. The absorbent composite 50 is secured to the body panel base webs 120, 148 by bonding and the like, or by other devices known to those of skill in the art.

In one embodiment, where the front and rear body panel webs are separate from one another and from the absorbent composite, leg openings are formed between the successive cross direction absorbent composites, which define the crotch portions and which are spaced along the machine direction. In an alternative embodiment, where the outer cover defines in part the front and rear body panels, a die cutter successively cuts leg openings in the outer cover between the absorbent composites to form the ladder type configuration with a plurality of crotch portions. The cutter can also shape one or both of the body panel webs.

A landing member, made of a landing material, can be applied to the front body panel, preferably a garment side surface thereof, as it moves therewith in a machine direction. The landing material can be made of any of the above-described materials, including for example a point unbonded, nonwoven material or a spunbond nonwoven material. The landing material can also be made of various known loop materials as described above. Alternatively, if the fastener member is configured as a tape, the landing material preferably made of various known materials that interface with such tape.

Referring to FIGS. 5, 6, 9–12 and 19 at zone A2, a plurality of discrete fastener pieces 450 are successively applied to the body side surface of the rear body panel web 148 along the machine direction. Each fastener piece includes a first and second end 456, 454 spaced along the machine direction. In one preferred embodiment, the fastener piece 450 includes a carrier material 452 and a refastenable portion 51 disposed thereon proximate each end on a first side thereof. In one preferred embodiment, any elastic elements in the body panels are deadened or deactivated beneath the attachment of the fastener piece. In an alternative preferred embodiment, the fastener piece 450 does not include a carrier member, but rather is configured entirely of a refastenable material, for example as a strip of refastenable material, having a refastenable portion, for example an array of hooks, formed on a first side thereof. Preferably, the refastenable portion(s) 51 of each fastener piece are releasably engaged with the bodyside surface of the rear body panel web.

Referring to zone A3, the first side of each fastener piece 450 is fixedly secured, preferably by bonding such as ultrasonic bonding, to the body side surface of the body panel web 148 at an attachment location 45 extending along a cross direction between the refastenable portions 51, or approximately midway of the fastener pieces 450.

Referring to zone A4 of FIGS. 5–6 and 9–12, the crotch portion 462 is folded such that the rear body panel base web 148 overlies and faces the front body panel base web 120. Likewise at zone A4 of FIG. 20, the crotch portion of the chassis is folded such that the end portion overlies or faces the rear body panel. The front and/or rear body panel webs 120, 148 and fastener pieces 450 are then successively cut with a cutter along the cross direction at the attachment locations 45 so as to form a plurality of discrete body panels 4, 6 and refastenable absorbent garments, with each of the rear body panels 6 having a fastener member 42 secured to the opposite sides 28, 410 thereof. In an alternative embodiment, the front and rear body panels also can be cut before the crotch portion if folded. The cutter can be a knife and anvil cutter, a laser, or water jet cutter, or any other cutter known to those of skill in the art. Each of the pair of fastener members 42 formed from a single fastener piece 450 are attached proximate to adjacent side edges 28 of successive body panels 6 and absorbent garments in the stream of such body panels and garments. In this embodiment, the absorbent product is formed as an "open" product, with the fastener members 42 folded over and releasably secured to the body side surface 10 of the rear body panel 6. When used, the fastener members 42 are disengaged from the rear body panel, rotated about the attachment location 45 and releasably engaged with the garment side surface 12 of the front body panel 4 to secure the garment on the user.

The lateral width of the fastener pieces can be shortened or lengthened to provide a smaller or larger absorbent garment respectively without altering the distance or machine pitch between the cross direction cuts. As such, the process can be easily changed to manufacture various size garments without having to reconfigure the various cutters and other apparatus. For example, a first group of fastener pieces, and in particular a first group of carrier members has a greater width than a second group of fastener pieces, and in particular a second group of carrier members. Accordingly, absorbent garments made with the first group of fastener pieces, although having the same body panels as absorbent garments made with the second group of fastener pieces, can accommodate user's having a larger waist.

Referring to FIG. 6, a plurality of extension pieces 500 are successively applied to the front body panel web in a similar fashion as the fastener pieces. In particular, each extension piece 500 is successively fixedly secured to the body side surface 10 of the front body panel web 120 at an attachment location 484, which locations are preferably aligned with the attachment locations 45. Alternatively, the extension piece can be secured to the garment side surface of the front body panel. After the crotch portion is folded, as explained above, the extension piece 500 is successively cut with the front body panel web 120 along the cross direction at the attachment location 484 to form a pair of extension members 414 attached respectively to successive front body panels 4 and absorbent garments in the stream of plurality of such body panels and garments. The extension pieces can be folded over the front body panel, along either of the body side or garment side surface thereof, prior to use by the user.

Referring to zone A2 of FIGS. 7 and 8, the plurality of discrete fastener pieces 450 are successively applied to the garment side surface of the front body panel web 120 along the machine direction. Each fastener piece includes a first and second end 456, 454 spaced along the machine direction. Fastener piece 450 includes a carrier material 452 and a refastenable portion 51 disposed thereon proximate each end on a first side thereof. In one preferred embodiment, the entire fastener piece 450 is configured with a refastenable portion formed on a first side thereof. Preferably, the refastenable portion(s) 51 of each fastener piece are releasably engaged with the garment side surface of the front body panel web. In one embodiment, the first side of each fastener piece is then fixedly secured, preferably by bonding such as ultrasonic bonding, to the garment side surface of the body panel web at an attachment location extending along a cross direction between the refastenable portions, or approximately midway of the fastener pieces. An exemplary ultrasonic bonder is the rotating horn and anvil type ultrasonic bonder disclosed in U.S. Pat. No. 5,660,679, the entirety of which is hereby incorporated herein by reference. Another type of ultrasonic bonder is disclosed in U.S. Pat. No. 6,123,792, the entire disclosure of which is hereby incorporated herein by reference. It should be understood that the fastener pieces can be fixedly secured to the body panel web using adhesive bonds, thermal bonds, stitching and other attachment devices known to those of skill in the art.

Referring to zone A4 of FIGS. 7 and 8, the crotch portion is folded such that the rear body panel base web 148 overlies and faces the front body panel base web 120. Side seams 39 are formed by attaching the side edges 24 and 28 of the front and rear body panels, preferably by ultrasonic bonding, or with adhesive bonds, stitching or other suitable means known to those skilled in the art. In one preferred embodiment, shown in FIGS. 7 and 8, the crotch portion 462 is folded prior to fixedly securing the fastener piece 450 to the front body panel web 120, with the fastener piece 450 releasably connected to the garment side surface 12 of the front body panel web 12 by way of the releasable connection between the refastenable portion and the front body panel, or landing member disposed thereon. The fastener piece 450 is simultaneously bonded to the front body panel web 120 at location 45 as the front body panel web 120 is bonded or connected to the rear body panel web 148, preferably by ultrasonic bonding. Of course, it should be understood that the fastener piece can be first bonded or connected to one or the other of the front and rear body panels prior to folding, and that the front body panel can be connected to the rear body panel along the same location after the crotch portion is folded. The connection between the front and rear body panels can also serve to create an additional bond between the fastener piece and either the front or rear body panel.

At zone A5, a cross direction cut 150 is made through the side seam 39 and attachment location 45 to separate the refastenable absorbent garments. As explained above, the side seam can also be omitted. The cut can be made with a knife and anvil cutter, or other suitable cutter as explained above. The refastenable absorbent garments can thereafter be folded and packaged for sale to the end user. The plurality of discrete body panels and refastenable absorbent garments each have a front body panel with a fastener member 42 secured to the opposite sides thereof. Each of the pair of fastener members 42 formed from a single fastener piece are attached to adjacent side edges of successive body panels and absorbent garments in the stream of such body panels and garments. In this embodiment, the absorbent product is formed as pant type product.

As shown in FIG. 8, a pair of cross direction cuts 140 spaced along the machine direction are successively made in the front body panel web with a cutter to form the lines of weakness 37, preferably spaced on each side of the attachment location 45 and side seam 39, but between the attachment location 45 and the area where the refastenable portion 51 is engaged with the front body panel, or landing member secured thereto. Preferably, the cuts are formed as perforations or like penetrations that do not completely separate the web. Referring to zone A1, preferably the cross direction cuts 140 are made prior to the application of the fastener piece 450 to the front body panel web 120. In the embodiment wherein the entirety of the fastener piece includes a refastenable portion, the line of weakness is positioned between the ends of the fastener member, and more preferably between the ends of the fastener piece and a midpoint of the fastener piece. Preferably, engagement between the refastenable portion 51 of the fastener material and the middle portion 33 of the front body panel, whether it be of a hook and loop engagement or an adhesive engagement, is the only type of engagement between those two members. Alternatively, one or more secondary, breakable bonds can be formed between the fastener member and the landing member or front body panel on the inboard side of the line of weakness. The breakable bond can be broken when the garment is put into use, for example, when it is desired to use the refastenable feature of the garment.

Referring to FIGS. 13–15, the rear body panel web 148 and fastener pieces 450 are successively cut along the cross direction so as to form a plurality of discrete body panels 6 and refastenable absorbent garments, with each of the rear body panels having one or more fastener members 42 formed along the opposite sides thereof. The body panel web and fastener pieces can be cut with a rotary die cutter, a knife and anvil cutter, or any other cutter suitable for such a cut as known by those of skill in the art. Preferably, where a plurality of tab members 47 are spaced longitudinally along the base web, as shown for example in FIGS. 13 and 14, a serpentine cross direction cut 624 is made through the body panel web 148 and fastener pieces 450 to form a plurality of fastener tabs 47. Preferably, the cut 624 forms mirror image tabs 47 in the successive absorbent garments, with waste material 620 between each set of tab members being collected and recycled. Each of the pair of fastener members 42 formed from the fastener pieces 450 are formed along adjacent side edges 28 of successive body panels and absorbent garments in the stream of such body panels and garments. In this embodiment, the absorbent product is formed as an "open" product. When used, the fastener members are releasably engaged with the garment side surface 12 of the front body panel 4 to secure the garment on the user.

Various aspects of the process for making the absorbent garment are further disclosed in U.S. application Ser. No. 09/834,870, filed Apr. 13, 2001, and entitled "Multiple Component Web," U.S. application Ser. No. 09/834,875, filed Apr. 13, 2001 and entitled "Method of Assembling Personal Care Absorbent Article," U.S. application Ser. No. 09/834,869, filed Apr. 13, 2001, and entitled "Pant-Type Personal Care Articles, and Methods of Making and Using Such Personal Care Articles," U.S. application Ser. No.

09/834,787, filed Apr. 13, 2001 and entitled "Methods of Changing Size of Pant-Type Personal Care Articles Outputted from a Manufacturing Process," and U.S. application Ser. No. 09/834,682, filed Apr. 13, 2001 and entitled "Passive Bonds For Personal Care Article," the entire disclosures of which are hereby incorporated by reference.

In other aspects, the absorbent garment and the process for making the absorbent garment are further disclosed in U.S. application Serial No. 60/303,307, filed Jul. 5, 2001, and entitled "Refastenable Absorbent Garment," the entire disclosure of which is hereby incorporated by reference.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A method for manufacturing a refastenable absorbent garment comprising:
   moving a continuous body panel web in a machine direction;
   successively fixedly securing a plurality of discrete fastener pieces to said body panel web, wherein said plurality of fastener pieces are spaced along said machine direction, and wherein each of said fastener pieces comprises a first and second end spaced along said machine direction; and
   successively cutting said body panel web and each of said fastener pieces along a cross direction at a location between said first and second ends of each of said fastener pieces and thereby forming a plurality of discrete body panels each comprising opposite side edges and a plurality of pairs of fastener members, wherein said fastener members in each of said pairs of fastener members are fixedly secured to one of said plurality of said body panels and a next successive body panel and wherein each of said plurality of body panels forms part of and is associated with a corresponding individual refastenable absorbent garment.

2. The method of claim 1 wherein each of said plurality of fastener pieces comprises a refastenable portion formed proximate at least both of said first and second ends thereof.

3. The method of claim 2 further comprising releasably engaging said body panel web with said refastenable portions of each of said plurality of said fastener pieces.

4. The method of claim 3 wherein said successively cutting said body panel web and each of said fastener pieces along said cross direction at said location between said first and second ends of said fastener pieces comprises successively cutting said body panel web at a plurality of first locations, and further comprising successively cutting said body panel web along said cross direction at plurality of second locations between each of said releasable engagements of said body panel web with said refastenable portions of said fastener pieces and each of said fixed securements of said body panel web with said fastener pieces.

5. The method of claim 4 wherein said successively cutting said body panel web at said second locations comprises successively cutting said body panel web at said second locations prior to said fixedly securing said plurality of fastener pieces to said body panel web.

6. The method of claim 4 wherein said successive cutting of said body panel web at said second locations comprises successively perforating said body panel web at said second locations.

7. The method of claim 6 wherein said body panel web comprises a front body panel web.

8. The method of claim 2 wherein said plurality of fastener pieces each comprise a carrier member supporting said refastenable portion.

9. The method of claim 8 wherein at least a portion of said carrier member is elasticized.

10. The method of claim 8 wherein said each of said carrier members has a lateral width, and further comprising altering said width of said carrier members, wherein said carrier members comprise a first group of carrier members having a first width and a second group of carrier members having a second width, wherein said first width is greater than said second width.

11. The method of claim 2 wherein said refastenable portion comprises a hook material.

12. The method of claim 2 wherein said fastener pieces each comprise a first and second side, wherein said first side is fixedly secured to said body panel web and wherein said second side comprises said refastenable portion, wherein said refastenable portion faces away from said body panel web.

13. The method of claim 12 wherein an entirety of said first side is fixedly secured to said body panel web.

14. The method of claim 2 wherein said fastener pieces each comprise a first and second side, wherein said first side faces and comprises a portion that is fixedly secured to said body panel web and wherein said first side further comprises said refastenable portion.

15. The method of claim 1 wherein said body panel web comprises a front body panel web and further comprising moving a second body panel web in said machine direction.

16. The method of claim 1 wherein said body panel web comprises a front body panel web.

17. The method of claim 1 wherein said body panel web comprises a first body panel web and further comprising moving a second continuous body panel web and a plurality of discrete crotch portions in said machine direction, wherein said plurality of crotch portions are spaced along said machine direction and extend between said continuous first and second body panel webs.

18. The method of claim 17 further comprising folding said crotch portion, wherein said continuous first and second body panel webs face each other.

19. The method of claim 18 further comprising successively attaching said first and second body panel webs at a plurality of cross direction attachment locations spaced along said machine direction and thereby forming a plurality of cross direction side seams spaced along said machine direction.

20. The method of claim 19 wherein said successively attaching said first and second body panel webs along said cross direction and said successively fixedly securing said plurality of fastener pieces to said first body panel web are performed simultaneously.

21. The method of claim 19 wherein said successively cutting said body panel web and each of said fastener pieces along said cross direction comprises successively cutting said first and second body panel webs and each of said fastener pieces along said cross direction at said side seams.

22. The method of claim 17 further comprising successively fixedly securing a plurality of discrete extension panels to said second body panel web at an attachment location, and successively cutting said second body panel web and said discrete extension panels along said cross direction at said attachment location and thereby forming a plurality of discrete second body panels each comprising opposite side edges and a plurality of extension members each secured to said second body panel along one of said opposite side edges.

23. The method of claim 1 wherein said successively cutting said body panel web and each of said fastener pieces along said cross direction comprises making a serpentine cut along said cross direction.

24. A method for manufacturing a refastenable absorbent garment comprising:

moving a body panel web in a machine direction;

successively applying a plurality of discrete fastener pieces to said body panel web, wherein said fastener pieces are spaced along said machine direction, and wherein each of said plurality of fastener pieces comprises a first and second end spaced along said machine direction and a refastenable portion formed proximate at least both of said first and second ends;

releasably engaging said body panel web with said refastenable portions of each of said plurality of said discrete fastener pieces;

fixedly securing each of said plurality of said discrete fastener pieces to said body panel web at an attachment location between said refastenable portions formed proximate said at least both of said first and second ends; and successively cutting said body panel web and each of said fastener pieces along a cross direction at said attachment location and thereby forming a plurality of discrete body panels each comprising opposite side edges and a plurality of pairs of fastener members each comprising a first end fixedly secured to one of said body panels adjacent one of said opposite side edges and a second end comprising said refastenable portion releasably engaged with said one of said discrete body panels inboard of said one of said opposite side edges.

25. The method of claim 24 further comprising successively perforating said body panel web along said cross direction at plurality of breakable locations between each of said releasable engagements of said body panel web with said refastenable portions of said fastener pieces and each of said attachment locations of said body panel web with said fastener pieces.

26. The method of claim 25 wherein said successively perforating said body panel web at said breakable locations comprises successively perforating said body panel web at said breakable locations prior to said fixedly securing said plurality of fastener pieces to said body panel web.

27. The method of claim 26 wherein said body panel web comprises a front body panel web.

28. The method of claim 24 wherein said fastener pieces each comprise a carrier member supporting said refastenable portion.

29. The method of claim 28 wherein at least a portion of said carrier member is elasticized.

30. The method of claim 28 wherein said each of said carrier members has a lateral width, and further comprising altering said width of said carrier members, wherein said carrier members comprise a first group of carrier members having a first width and a second group of carrier members having a second width, wherein said first width is greater than said second width.

31. The method of claim 24 wherein said refastenable portion comprises a hook material.

32. The method of claim 24 wherein said fastener pieces each comprise a first and second side, wherein said first side faces and comprises a portion that is fixedly secured to said body panel web and wherein said first side further comprises said refastenable portion.

33. The method of claim 24 wherein said body panel web comprises a first body panel web and further comprising moving a second continuous body panel web and a plurality of discrete crotch portions spaced along said machine direction and extending between said continuous first and second body panel webs in said machine direction.

34. The method of claim 33 further comprising folding said crotch portion, wherein said continuous first and second body panel webs face each other.

35. The method of claim 34 wherein said attachment location is a first location and further comprising successively attaching said first and second body panel webs at a second cross direction attachment location and thereby forming a plurality of cross direction side seams spaced along said machine direction.

36. The method of claim 35 wherein said successively attaching said first and second body panel webs at said second attachment location and said successively fixedly securing said plurality of fastener pieces to said first body panel web at said first attachment location are performed simultaneously, and wherein said first and second attachment locations are coextensive.

37. The method of claim 35 wherein said successively cutting said first body panel web and each of said fastener pieces along said cross direction comprises successively cutting said first and second body panel webs and each of said fastener pieces along said cross direction at said side seams.

38. The method of claim 33 wherein said attachment location is a first attachment location and further comprising successively fixedly securing a plurality of discrete extension panels to said second body panel web at a plurality of second attachment locations, and successively cutting said second body panel web and said discrete extension panels at said second attachment locations and thereby forming a plurality of discrete second body panels each comprising opposite side edges and a plurality of extension members each secured to said second body panel along one of said opposite side edges.

39. The method of claim 24 wherein said successively cutting said body panel web and each of said fastener pieces at said attachment location comprises making a serpentine cut along said cross direction.

* * * * *